(12) United States Patent
Cam et al.

(10) Patent No.: US 10,350,258 B2
(45) Date of Patent: Jul. 16, 2019

(54) COMPOSITIONS AND METHODS FOR THE TREATMENT OF PLAQUES AND TANGLES IN HUMANS AND ANIMALS

(71) Applicant: Cognitive Clarity Inc., Lynnwood, WA (US)

(72) Inventors: Judy Cam, Bellevue, WA (US); Thomas Lake, Snohomish, WA (US); Qubai Hu, Kirkland, WA (US); Joel Cummings, Seattle, WA (US); Alan D Snow, Lynnwood, WA (US)

(73) Assignee: Cognitive Clarity Inc., Edmonds, WA (US)

( * ) Notice: Subject to any disclaimer, the term of this patent is extended or adjusted under 35 U.S.C. 154(b) by 0 days.

(21) Appl. No.: 15/669,443

(22) Filed: Aug. 4, 2017

(65) Prior Publication Data

US 2017/0333512 A1 Nov. 23, 2017

Related U.S. Application Data

(63) Continuation of application No. 15/053,572, filed on Feb. 25, 2016.

(60) Provisional application No. 62/126,026, filed on Feb. 27, 2015, provisional application No. 62/170,822, filed on Jun. 4, 2015.

(51) Int. Cl.
*A61K 36/82* (2006.01)
*A61K 36/74* (2006.01)

(52) U.S. Cl.
CPC ............. *A61K 36/82* (2013.01); *A61K 36/74* (2013.01)

(58) Field of Classification Search
None
See application file for complete search history.

(56) References Cited

U.S. PATENT DOCUMENTS

| 6,264,994 B1 * | 7/2001 | Castillo | A61K 31/215 424/725 |
| 6,346,280 B1 * | 2/2002 | Castillo | A61K 31/215 424/725 |
| 6,939,570 B1 * | 9/2005 | Snow | A61K 31/215 424/725 |
| 7,148,001 B2 | 12/2006 | Castillo et al. | |
| 2001/0055630 A1 | 12/2001 | Castillo et al. | |
| 2007/0190075 A1 * | 8/2007 | Suzuki | A61K 8/97 424/195.17 |
| 2012/0053138 A1 | 3/2012 | Jia et al. | |
| 2015/0017108 A1 | 1/2015 | Wang | |
| 2016/0250273 A1 | 9/2016 | Cam | |

FOREIGN PATENT DOCUMENTS

| WO | 9851302 | 11/1998 |
| WO | WO-00/30666 A1 | 6/2000 |
| WO | WO-00/33659 A1 | 6/2000 |

OTHER PUBLICATIONS

Chan et al., "Favorable effects of tea on reducing the cognitive deficits and brain morphological changes in senescence-accelerated mice." Journal of Nutritional Science and Vitaminology, 2006, vol. 52, pp. 266-273.

International Search Report and Written Opinion on PCT/US2016/019572, dated Aug. 29, 2016.

Kurihara et al., "Inhibitory effect of oolong tea on the oxidative state of low density lipoprotein (LDL)." Biological and Pharmaceutical Bulletin, 2003, vol. 26, No. 5. pp. 739-742.

Sandoval et al., "Anti-inflammatory and antioxidant activities of cat's claw (*Uncaria tomentosa* and *Uncaria guianensis*) are independent of their alkaloid content," Phytomedicine, 2002, vol. 9, No. 4, pp. 325-337.

Amen, "12 prescriptions for creating a brain healthy life." Retrieved Jun. 23, 2016 from: www.amenclinics.com/cybcyb/12-prescriptions-for-creating-a-brain-healthy-life.

Arai et al., "Argyorophilic glial inclusions in the midbrain of patients with Parkinson's disease and diffuse Lewy body disease are immunopositive for NACP/.alpha.-synuclein." Neurosc. Lett. 259: 83-86 (1999).

Askanas et al., Ann. Neurol. 43: 521-560, 1993.

Barghorn et al., "Purification of Recombinant Tau Protein and Preparation of Alzheimer-Paired Helical Filaments In Vitro," Methods Mol. Biol. 299: 35-51 (2005).

Breslow, "New: 87 deceased NFL players test positive for brain disease." Frontline, Jan. 9, 2016. Retrieved Jun. 23, 2016, from http://www.pbs.org/wgbh/frontline/article/new-87-deceased-nfl-players-test-positive-for-brain-disease/.

Capucchio et al., "Parenchymal and vascular lesions in ageing equine brains: histological and immunohistochemical studies." J. Comp. Pathol. 142(1): 61-73 (2010).

Chen et al., "A learning deficit related to age and .beta.-amyloid plaques in a mouse model of Alzheimer's disease." Nature 408: 975-979 (2000).

Dumont et al., "Bezafibrate administration improves behavioral deficits and tau pathology in P3015 mice," Human Molecular Genetics 21: 5091-5105 (2012).

Flood et al., "Amnestic effects in mice of four synthetic peptides homologous to amyloid .beta. protein from patients with Alzheimer disease," Proc. Natl. Acad. Sci. USA 88(8): 3363-3366 (1991).

Flood et al., "An amyloid I3-protein fragment, A13[12-28], equipotently impairs post-training memory processing when injected into different limbic system structures." Brain Res. 663(2): 271-276 (1994).

Friedhoff et al., "Rapid Assembly of Alzheimer-like Paired Helical Filaments from Microtubule-Associated Protein Tau Monitored by Fluorescence in Solution," Biochemistry 37(28): 10223-10230 (1996).

Games et al., "Alzheimer-type neuropathology in transgenic mice overexpressing V717F .beta.-amyloid precursor protein," Nature 373: 523-527(1995).

Giannakopoulos et al., "Tangle and neuron numbers, but not amyloid load, predict cognitive status in Alzheimer's disease." Neurology 60(9): 1495-1500 (2003).

(Continued)

*Primary Examiner* — Susan Hoffman
(74) *Attorney, Agent, or Firm* — Foley & Lardner LLP; Paul S. Hunter; Jennifer Best-Martin (57) ABSTRACT

Methods of treating the formation, deposition, accumulation, or persistence of beta-amyloid containing plaques and tau protein containing tangles including the step of treating the plaques or tangles with an effective amount of a composition comprising an *Uncaria tomentosa* extract and an oolong tea extract. Compositions containing an *Uncaria tomentosa* extract in combination with an oolong tea extract.

5 Claims, 6 Drawing Sheets

(56) References Cited

OTHER PUBLICATIONS

Glenner and Wong, "Alzheimer's disease: initial report of the purification and characterization of a novel cerebrovascular amyloid protein." Biochem. Bio phys. Res. Comm. 120(3): 885-890 (1984).
Grundke-Iqbal et al., "Abnormal phosphorylation of microtubule-associated protein T (tau) in Alzheimer cytoskeletal pathology," Proc. Natl. Acad. Sci. USA 83(13): 4913-4917 (1986).
Gunn-Moore et al., "Cognitive dysfunction and the neurobiology of ageing in cats." J Small Anim. Pract. 48: 546-553 (2007).
Haass et al., "The Swedish mutation causes early-onset Alzheimer's disease by bold beta-secretase cleavage within the secretary pathway." Nature Med. 1: 1291-1296 (1995).
Hardy, "Framing beta-amyloid." Nature Genet 1 : 223-234 (1992).
Harrigan et al., "Beta amyloid is neurotoxic in hippocampal slice cultures," Neurobiol. Aging 16: 779-789 (1995).
Hsiao et al., "Correlative memory deficits, Abeta elevation, and amyloid plaques in transgenic mice." Science 274 (5284): 99-102 (1996).
Janus et al., "A .beta. peptide immunization reduces behavioral impairment and plaques in a model of Alzheimer's disease." Nature 408: 979-982 (2000).
Karlnoski et al., "Suppression of amyloid deposition leads to long-term reductions in Alzheimer's pathologies in Tg2576 mice." J. Neurosc. 29(15): 4964-4971 (2009).
Kosik et al., "Microtubule-associated protein tau (tau) is a major antigenic component of paired helical filaments in Alzheimer disease." Proc. Natl. Acad. Sci. USA 83(11): 4044-4048 (1986).
Lee et al., "A68: a major subunit of paired helical filaments and derivatized forms of normal Tau." Science 251 (4994): 675-678 (1991).
Lee et al., "Neurodegenerative tauopathies." Ann. Rev. Neurosci. 24: 1121-1159 (2001).
Levine, "Thioflavine T interaction with amyloid I3-sheet structures," Amyloid 2(1 ): 1-6 (1995).
Levine, "Thioflavine T interaction with synthetic Alzheimer's disease beta-amyloid peptides: detection of amyloid aggregation in solution." Protein Sci. 2(3): 404-410 (1993).
Mandybur, J. "Cerebral amyloid angiopathy: the vascular pathology and complications." Neuropath. Exp. Neurol. 45 (1): 79-90 (1986).
Masters et al., "Amyloid plaque core protein in Alzheimer disease and Down syndrome." Proc. Natl. Acad. Sci. USA 82(12): 4245-4249 (1985).
Morgan et al., "A .beta. peptide vaccination prevents memory loss in an animal model of Alzheimer's disease." Nature 408(6815): 982-985 (2000).
Murrell et al., "A mutation in the amyloid precursor protein associated with hereditary Alzheimer's disease." Science 254(5028): 97-99 (1991).
Naiki and Nakakuki, "First-order kinetic model of Alzheimer's beta-amyloid fibril extension in vitro." Lab. Invest. 74 (2): 374-383 (1996).
Nakai et al., "Kinetic analysis of amyloid fibril polymerization in vitro." Lab Invest 65(1 ): 104-110 (1991).
Nakamura et al., "Histopathological studies of senile plaques and cerebral amyloidosis in cynomolgus monkeys." J. Med. Primatol. 27(5): 244-252 (1998).
Nakamura et al., "Senile plaques in an aged two-humped (Bactrian) camel (*Camelus bactrianus*)." Acta Neuropath. 90(4): 415-418 (1995).
Nakamura et al., "Senile plaques in very aged cats." Acta Neuropath. 91: 437-439 (1996).
Oddo et al., "Reduction of soluble Abeta and tau, but not soluble Abeta alone, ameliorates cognitive decline in transgenic mice with plaques and tangles." J. Biol. Chem. 281 (51): 39413-39423 (2006).
Omalu et al., "Emerging histomorphologic phenotypes of chronic traumatic encephalopathy in American athletes." Neurosurgery 69(1 ): 173-183 (2011 ).
Papaioannou et al., "Immunohistochemical investigation of the brain of aged dogs. I. Detection of neurofibrillary tangles and of 4-hydroxynoneal protein, an oxidating damage product, in senile plaques." Amyloid 8(1): 11-21 (2001).
Pardridge et al., "Amyloid Angiopathy of Alzheimer's Disease: Amino Acid Composition and Partial Sequence of a 4,200-Dalton Peptide Isolated from Cortical Microvessels." J. Neurochem. 49(5): 1394-1401 (1987).
Pike et al., "In vitro aging of .beta.-amyloid protein causes peptide aggregation and neurotoxicity," Brian Res. 563 (1-2): 311-314 (1991).
Pike et al., "Structure-Activity Analysis of .beta.-Amyloid Peptides: Contributions of the .beta.25-35 Region to Aggregation and Neurotoxicity." J. Neurochem. 64: 253-265 (1995).
Pollan EN et al., "Pathology and biology of the Lewy body.," J. Neuropath. Exp. Neurol. 52(3): 183-191 (1993).
Rajput et al., "Parkinsonism, Lrrk2 G2019S, and tau neuropathology," 67(8): 1506-1508 (2006).
Santacruz et al., "Tau suppression in a neurodegenerative mousel model improves memory function." NIH-PA Author Manuscript (2006), also published in Science 309(5733): 476-481 (2005).
Santpere and Ferrer, :LRRK2 and neurodegeneration. Acta Neuropathol. 117: 227-245 (2009).
Schenk et al., "Immunization with amyloid-.beta. attenuates Alzheimer-disease like pathology in PDAPP mouse." Nature 400: 173-177 (1999).
Spillantini et al., ".alpha.-Synuclein in filamentous inclusions of Lewy bodies from Parkinson's disease and dementia with Lewy bodies." Proc. Natl. Acad. Sci. USA 95(11): 6469-6473 (1998).
Tanzi et al., "Protease inhibitor domain encoded by an amyloid protein precursor mRNA associated with Alzheimer's disease," Nature 331: 528-530 (1988).
Uchida et al., "Amyloid angiopathy with cerebral hermorrhage and senile plaque in aged dogs." Jpn. J. Vet. Sci. 52 (3): 605-611 (1990).
Uchida et al., "Senile plaques and other senile changes in the brain of an aged American black bear," Vet. Pathol. 32 (4): 412-414 (1995).
Van Broeckhoven et al., "Amyloid beta protein precursor gene and hereditary cerebral hemorrhage with amyloidosis (Dutch)." Science 248(4959): 1120-1122 (1990).
Vellas et al., "Long-term follow-up of patients immunized with AN1792: Reduced functional decline in antibody responders." Current Alz. Res. 6(2): 144-152 (2009).
Wakabayashi et al., "Accumulation ofa-synuclein/NACP is a cytopathological feature common to Lewy body disease and multiple system atrophy." Acta Neuropath. 96(5): 445-452 (1998).
WHO-I UIS Nomenclature Sub-Committee, "Nomenclature of amyloid and amyloidosis." Bull. WHO 71: 105-108 (1993).
Yanamandra et al., Anti-tau antibodies that block tau aggregate seeding in vitro markedly decreases pathology and improves cognition in vivo. Neuron 80(2): 402-414 (2013).
International Search Report and Written Opinion received in Singapore Application No. 11201706861Q dated Jul. 30, 2018.
Dotinga, R., Plaques, Tangles in Brain Don't Always Lead to Alzheimer's, https:/www.medicinenet.com/script/main/art.asp?articlekey?100750, dated May 27, 2009, (accessed Jan. 7, 2019).
Elder, et al., Transgenic Mouse Models of Alzheimer's Disease, 77(1):69-81 (2010).
Extended European Search Report dated Sep. 7, 2018 in EP Patent Application No. 16756363.4.
Stern, Y., Cognitive reserve in ageing and Alzheimer's disease, Lancet Neurol., 11(11):1006-1012 (2012).
Takeda, et al., Senescence-accelerated mouse (SAM): a novel murine model of senescence, 32(1-2):105-9 (1997) (Abstract Only).

* cited by examiner

Control  LOTE+PTI-00703 (0.1:1)

FIG. 2B

Control  LOTE+PTI-00703 (0.1:1)

FIG. 2C

Control  LOTE+PTI-00703 (1:1)

COMPOSITIONS AND METHODS FOR THE TREATMENT OF PLAQUES AND TANGLES IN HUMANS AND ANIMALS

CROSS REFERENCE TO RELATED APPLICATIONS

This application in a Continuation of U.S. patent application Ser. No. 15/053,572 filed Feb. 25, 2016 which claimed priority to U.S. PA 62/126,026 filed Feb. 27, 2015, and to U.S. PA 62/170,822 filed Jun. 4, 2015, each of which is hereby incorporated by reference.

TECHNICAL FIELD

The invention relates to blended compositions of plant extracts of *Uncaria tomentosa* and Oolong tea and methods for treating "plagues and tangles" that accumulate in the aging brain in amyloidosis and tauopathies in humans and animals (i.e. such as aged dogs and cats). In addition, the invention relates to the development of a nutraceutical blended composition consisting of a combination of a plant extract of *Uncaria tomentosa* and a specific Oolong tea, to prevent and treat traumatic brain injury (TBI), concussions (as observed in most athletes and the military/soldiers), single and repeated blows to the head, and chronic traumatic encephalopathy (CTE).

BACKGROUND

Amyloidosis and the Accumulation of Beta-Amyloid Plaques in the Brain of a Variety of Disorders Alzheimer's disease is characterized by the accumulation of a 39-43 amino acid peptide termed the beta-amyloid protein or AP, in a fibrillary form, existing as extracellular amyloid plaques and as amyloid within the walls of cerebral blood vessels. Fibrillar A13 amyloid deposition in Alzheimer's disease is believed to be detrimental to the patient and eventually leads to toxicity and neuronal cell death, a characteristic hallmark of Alzheimer's disease. Accumulating evidence implicates amyloid, and more specifically, the formation, deposition, accumulation and/or persistence of AP fibrils, as a major causative factor of Alzheimer's disease pathogenesis. In addition, besides Alzheimer's disease, a number of other amyloid diseases involve formation, deposition, accumulation and persistence of AP fibrils, including Down's syndrome, disorders involving congophilic angiopathy, such as but not limited to, hereditary cerebral hemorrhage of the Dutch type, inclusion body myositosis, dementia pugilistica, cerebral (3-amyloid angiopathy, dementia associated with progressive supranuclear palsy, dementia associated with cortical basal degeneration and mild cognitive impairment.

The amyloid diseases (amyloidosis) are classified according to the type of amyloid protein as well as the underlying disease. Amyloid diseases have a number of common characteristics including each amyloid consisting of a unique type of amyloid protein. The amyloid diseases include, but are not limited to, the amyloid associated with Alzheimer's disease, Down's syndrome, Canine Dysfunction syndrome (CDS), Canine Cognitive Dysfunction (CCD), as seen in aged animals such as dogs and cats, hereditary cerebral hemorrhage with amyloidosis of the Dutch type, dementia pugilistica, inclusion body myositosis (Askanas et al., Ann. Neurol. 43:521-560, 1993) and mild cognitive impairment (where the specific amyloid is referred to as beta-amyloid protein or Aβ), the amyloid associated with chronic inflammation, various forms of malignancy and Familial Mediterranean Fever (where the specific amyloid is referred to as AA amyloid or inflammation-associated amyloidosis), the amyloid associated with multiple myeloma and other B-cell dyscrasias (where the specific amyloid is referred to as AL amyloid), the amyloid associated with type 2 diabetes (where the specific amyloid is referred to as amylin or islet amyloid polypeptide or IAPP), the amyloid associated with the prion diseases including Creutzfeld-Jakob disease, Gerstamann-Straussler syndrome, kuru and animal scrapie (where the specific amyloid is referred to as PrP amyloid), the amyloid associated with long-term hemodialysis and carpal tunnel syndrome (where the specific amyloid is referred to as α2-microglobulin amyloid), the amyloid associated with senile cardiac amyloidosis and Familial Amyloidotic Polyneuropathy (where the specific amyloid is referred to as transthyretin or prealbumin), and the amyloid associated with endocrine tumors such as medullary carcinoma of the thyroid (where the specific amyloid is referred to as variants of procalcitonin). In addition, the α-synuclein protein which forms amyloid-like fibrils, and is Congo red and Thioflavin S positive (specific stains used to detect amyloid fibrillary deposits), is found as part of Lewy bodies in the brains of patients with Parkinson's disease, Lewy body disease (Lewy in Handbuch der Neurologie, M. Lewandowsld, ed., Springer, Berlin pp. 920-933, 1912; Pollanen et al, J. Neuropath, Exp. Neurol. 52:183-191, 1993; Spillantini et al, Proc. Natl. Acad. Sci. USA 95:6469-6473, 1998; Arai et. al, Neurosc, Lett. 259:83-86, 1999), multiple system atrophy (Wakabayashi et al, Acta Neuropath. 96:445-452, 1998), dementia with Lewy bodies, and the Lewy body variant of Alzheimer's disease. For purposes of this disclosure, Parkinson's disease, due to the fact that fibrils develop in the brains of patients with this disease (which are Congo red and Thioflavin S positive, and which contain predominant beta-pleated sheet secondary structure), is now regarded as a disease that also displays the characteristics of an amyloid-disease.

Amyloid as a Therapeutic Target for Alzheimer's Disease

Alzheimer's disease is characterized by the deposition and accumulation of a 39-43 amino acid peptide termed the beta-amyloid protein, Aβ or β/A4 (Glenner and Wong, Biochem. Biophys, Res, Comm. 120:885-890, 1984; Masters et al, Proc. Natl. Acad. Sci. USA 82:4245-4249, 1985; Husby et al, Bull, WHO 71:105-108, 1993), Aβ is derived by protease cleavage from larger precursor proteins termed β-amyloid precursor proteins. (APPs) of which there are several alternatively spliced variants. The most abundant forms of the APPs include proteins consisting of 696, 751 and 770 amino acids (Tanzi et al. Nature 31:528-530, 19980.

The small Aβ peptide is a major component that makes up the amyloid deposits or "plaques" in the brains of patients with Alzheimer's disease. In addition, Alzheimer's disease is characterized by the presence of numerous neurofibrillary "tangles", consisting of paired helical filaments which abnormally accumulate in the neuronal cytoplasm (Grunddke-Iqbal et al, Proc. Natl. Acad. Sci. USA. 83:4913-4917, 1986; Kosik et al, Proc. Natl. Acad. Sci. USA 83:4044-4048, 1986; Lee et al, Science 251:675-678, 1991). The pathological hallmark of Alzheimer's disease is therefore the presence of both "plaques" and "tangles", with amyloid being deposited in the central core of the plaques. The other major type of lesion found in the Alzheimer's disease brain is the accumulation of amyloid in the walls of blood vessels, both within the brain parenchyma and in the walls of meningeal vessels that lie outside the brain. The amyloid deposits localized to the walls of blood vessels are referred to as cerebrovascular amyloid or congophilic angiopathy (Mandybur, J. Neuropath. Exp. Neurol. 45:79-90, 1986; Pardridge et al., J. Neurochem, 49:1394-1401, 1987).

For many years there has been an ongoing scientific debate as to the importance of "amyloid" in Alzheimer's disease, and whether the "plaques" and "tangles" characteristic of this disease were a cause or merely a consequence of the disease. Within the last few years, studies now indicate that amyloid is indeed a causative factor for Alzheimer's disease and should not be regarded as merely an innocent bystander. The Alzheimer's Aβ protein in cell culture has been shown to cause degeneration of nerve cells within short periods of time (Pike et al, Br. Res. 563:311-314, 1991; J. Neurochem. 64:253-265, 1995). Studies show that it is the fibrillary structure (consisting of a predominant β-pleated sheet secondary structure) characteristic of all amyloids that is responsible for the neurotoxic effects, Aβ has also been found to be neurotoxic in slice cultures of hippocampus (Harrigan et al, Neurobiol. Aging 16:779-789, 1995) and to induce nerve cell death in transgenic mice (Games et. al, Nature 373:523-527, 1995; Hsiao et al, Science 272:99-102, 1996). Injection of the Alzheimer's Aβ into rat brain also causes memory impairment and neuronal dysfunction (Flood et al, Proc. Natl. Acad. Sci. USA 88:3363-3366, 1991; Br. Res. 663:271-276, 1994).

Probably, the most convincing evidence that Aβ amyloid is directly involved in the pathogenesis of Alzheimer's disease comes from genetic studies. It was discovered that the production of Aβ can result from mutations in the gene encoding its precursor, β-amyloid precursor protein (Van Broeckhoven et al, Science 248:1120-1122, 1990; Murrell et al, Science 254:97-99, 1991; Haass et al, Nature Med. 1:1291-1296, 1995). The identification of mutations in the beta-amyloid precursor protein gene that cause early onset familial Alzheimer's disease is the strongest argument that amyloid is central to the pathogenic process underlying this diseases. Several reported disease-causing mutations have been discovered which demonstrate the importance of Aβ in causing familial Alzheimer's disease (reviewed in Hardy, Nature Genet. 1:223-234, 1992). All of these studies suggest that providing a therapy, drug or supplement to reduce, eliminate and/or prevent fibrillary Aβ formation, deposition, accumulation and/or persistence in the brains of humans and animals, well serve as an effective therapeutic.

The Accumulation of "Plaques and Tangles" in the Aging Human and Animal Brain

The human brain is the most complex organ in the universe. It weighs only 3 pounds, or about 2% of body weight. Yet is uses 20-30% of the calories consumed, 20% of the oxygen breathed, and 25% of the blood flow in the body; it consists of 85% water (Daniel G. Amen, M.D. 12 prescriptions for creating a brain healthy life. Source: www.amenclinics.com/cybcyb/12-prescriptions-for-creating-a-brain-healthy-life/). There are approximately 100 billion nerve cells (i.e. neurons) in the brain, and up to a quadrillion connections called synapses (ibid). The human brain as it ages, loses about 85,000 cortical neurons per day, or about one every second (Deepak Chopra, M.D. and Rudolph Tanzi, Ph.D. *Super Brain. Unleashing the Explosive Power of Your Mind to Maximize Health, Happiness, and Spiritual Well Being.* See///www.chopra.com/super-brain-by-deepak-chopra-rudolph-tanzi.) As the brain ages, starting in the 20's there is a slow but deliberate accumulation of two neurotoxic proteins. The first is the brain accumulation of an insoluble (aggregated) specific neurotoxic protein known as the "beta-amyloid protein" or Aβ. Beta-amyloid protein deposits in the form of "plaques" (looking like "meatballs" in the brain under a microscope), have been shown to be instrumental in killing healthy neurons that lead to a decline in hippocampus-dependent memory and cognition. Dr. Alan Snow and co-inventors developed patented methods to produce "plaques in a test-tube" (identical to what is seen in the human brain) and used these methods to screen for and identify natural "plaque-reducing" nutraceutical ingredients (U.S. Pat. No. 7,148, 001, which is incorporated herein by reference in its entirety).

The second neurotoxic protein that accumulates in the aging brain is known as the "tau protein" and forms twisted paired helical filaments known as "tangles." Neurofibrillary tangles accumulate inside neurons that causes them to die, and look like "dried spaghetti strands" under a microscope. Dr. Snow's laboratories developed proprietary methods to form "tangles" in a test-tube, and then used these assays to identify "tangle-inhibiting" nutraceutical ingredients (see examples below). Thus, in the aging brain, both "plaques and tangles" accumulate, causing neurons to die; connections between nerve cells (called synapses) to disintegrate; and memory and cognition to progressively decline. Compounds or agents able to disaggregate and reduce the accumulation of "plaques and tangles" have been shown to lead to memory improvement and a reduction in memory decline (Karlnoski et al. Suppression of amyloid deposition leads to long-term reductions in Alzheimer's pathologies in Tg2576 mice. J. Neurosc. 29:4964-4971, 2009; Vellas et al. Long-term follow-up of patients immunized with AN1792: Reduced functional decline in antibody responders. Current Alz. Res. 6:144-151, 2009; Morgan et al, Aβ peptide vaccination prevents memory loss in an animal model of Alzheimer's disease. Nature 408:982-985, 2000; Chen et al. A. learning deficit related to age and β-amyloid plaques in a mouse model of Alzheimer's disease. Nature 408:975-979, 2000; Janus et al. Aβ peptide immunization reduces behavioral impairment and plaques in a model of Alzheimer's disease. Nature 408:979-985, 2000; Schenk et al. Immunization with amyloid-β attenuates Alzheimer-disease like pathology in PDAPP mouse. Nature 400:173-177, 1999; Yanamandra et al. Anti-tau antibodies that block tau aggregate seeding in vitro markedly decreases pathology and improves cognition in vivo. Neuron 80:402-414, 2013; Dumont et al. Bezafibrate administration improves behavioral deficits and tau pathology in P3015 mice. Human Molecular Genetics 21:5091-5105, 2012; Oddo et al. Reduction of soluble Abeta and tau, but not soluble Abeta alone, ameliorates cognitive decline in transgenic mice with plaques and tangles. J. Biol. Chem. 281:39413-39423, 2006; Santacruz et al. Tau suppression in a neurodegenerative mouse model improves memory function. Science 309:476-481, 2005.)

The only difference between an aging brain that could lead to age-associated memory impairment (AAMI), then to mild-cognitive impairment (MCI), and potentially to Alzheimer's disease, and a brain that does not, is the number of "plaques and tangles" in the brain. Alzheimer's diseased brains are loaded with tens to hundreds of thousands of "plaques and tangles," per square millimeter, causing a marked increase in the death of neurons, leading to a loss of synapses (connections between neurons), and concurrent memory loss and cognitive decline.

Therefore, beta-amyloid and tau are two key proteins in the aging brain that accumulate as insoluble "plaques and tangles" that have been shown to be directly linked to memory loss and cognitive decline. There is currently no pharmaceutical drug that has been approved for reducing and removing both beta-amyloid protein "plaques" and tau protein-containing "tangles" in the brain.

The Accumulation of "Plaques" in the Aging Dog and Cat Brain

Dogs and cats also accumulate "plaques" (and, to a lesser extent, "tangles") in their brains as they age that are believed to contribute to memory decline and cognitive impairment. The same beta-amyloid protein (i.e. "plaques") and tau protein ("tangles") that accumulate in the human brain also accumulate in aged dogs (Papoiannou et al, Immunohistochemical investigation of the brain of aged dogs. I. Detection of neurofibrillary tangles and of 4-hydroxynonenal protein, an oxidative damage product, in senile plaques. Amyloid 8:11-21, 2001; Uchida et al, Amyloid angiopathy with cerebral hemorrhage and senile plaque in aged dogs. Nihon Juigaku Zasshi 52: 605-11, 1990) and cats (Gunn-Moore et al, Cognitive dysfunction and the neurobiology of ageing in cats. J Small Anim. Pract. 48: 546-53, 2007; Nakamura et al. Senile plaques in very aged cats. Acta Neuropath. 91:437-9, 1996).

Canine Cognitive Dysfunction (CCD) (also known as Cognitive Dysfunction Syndrome or CDS) is a disease prevalent in dogs (and cats) that exhibit symptoms of dementia or Alzheimer's disease as seen in humans. CCD creates pathological changes in the brain that slow the mental functioning of dogs (and cats) resulting in loss of memory, motor function and learned behaviors from training early in life. In the dog's and cat's brain, the culprit is again is the beta-amyloid protein or Aβ that forms "plaques" in the brain. As the dog ages, more and more "plaques" accumulate and nerve cells die. Although the initial symptoms of the disorders are mild, they gradually worsen over time, also known as "cognitive decline". Amyloid "plaques" occur in aged dogs at about five to seven years of age, and in cats of about ten years of age (which is proportional to their average lifespan of 15-20 years). In fact, clinical signs of cognitive dysfunction syndrome are found in 50% of dogs over the age of 11, and by the age of 15, 68% of dogs display at least one sign. Dogs will often find themselves confused in familiar places of the home, spending long periods of time in one area of the home, not responding to calls or commands, and experiencing abnormal sleeping patterns.

Beta-amyloid protein containing "plaques" also have been identified in the brains of other higher mammals including monkeys, bears, camels, and horses, (Nakamura et al, Histopathological studies of senile plaques and cerebral amyloidosis in cynomolgus monkeys. J Med Primatol. 27:244-52, 1998; Capucchio et al studies. J Comp Pathol 142:61-73, 2010; Nakamura et al, Senile plaques in an aged two-humped (Bactrian) camel (Camelus bactrianus), Acta Neuropathol 90: 415-8, 1995; Uchida et al. Senile plaques and other senile changes in the brain of an aged American black bear, Vet. Pathol. 32:412-4, 1995).

Tauopathies and "Tangles"

Tau was discovered in the mid-1970s as a microtubule associated protein (Weingarten, 1975). Besides being a stabilizer of microtubules in neurons and other cells, it has since been found to play important roles in cell differentiation, polarization and axonal transport. Normal tau is a soluble protein bound to microtubules, but in a series of neurodegenerative diseases, now known as tauopathies, tau accumulates as a pathogenic insoluble, fibrillar protein. These tau inclusions appear to modulate the severity of dementia and clinical features of these neurodegenerative diseases. Tauopathies include diseases such as Alzheimer's disease, frontotemporal lobar degeneration with tau inclusions (FTLD-tau) such as Pick's disease, progressive supranuclear palsy, and corticobasal degeneration, agyropbillic grain disease, some prion diseases, amyotrophic lateral sclerosis/parkinsonism-dementia complex, chrome traumatic encephalopathy, and some genetic forms of Parkinson's disease (V. M. Lee et al., Ann. Rev. Neurosci. 24:1121-1159, 2001; B. Omalu et al., Neurosurgery 69(1): 173-83, 2011; A. Rajput et al., Neurology 67:1506-1508, 2006; G. Santpere and I. Ferrer, Acta Neuropathol. 117: 227-246, 2009).

One of the most notable effects of increasing fibrillar tau in the brain is the gradual deterioration of short term memory; that is, the ability to recall immediately those memories only recently stored (P. Giannakopoulos et al., Neurology 60:1495-1500, 2003). As there is no treatment for these disorders, it is important to find a novel invention that could target this pathogenic protein and improve memory deficits.

"Tangles" Accumulate in Brain in Traumatic Brain Injury (TBI), Concussions, Head Trauma and Chronic Traumatic Encephalopathy (CTE)

Brain "tangles" consisting of tau protein also accumulate progressively in the brain following blows to the head and include concussions, head injury, post-traumatic stress disorder (PTSD), and blast-induced traumatic brain injury (seen in soldiers and military personnel who have traumatic head injuries induced by a single blast). The movie "concussion" and the NFL Players Association all discuss the dementia-type behavior that has been seen in athletes following repealed concussions and/or blows to the head (known as traumatic brain injury or TBI). Loss of consciousness is a clinical hallmark of concussion but is not required to make the diagnosis. Other symptoms include confusion, disorientation, unsteadiness, dizziness, headache, and visual disturbances.

The long-term consequences to traumatic brain injury is referred to as Chronic Traumatic Encephalopathy (CTE), which is form of tauopathy (i.e. tau protein containing "tangles" in the brain). CTE is a progressive degenerative disease found in people who have suffered repeated brain trauma including sub-concussive hits to the head that do not cause immediate symptoms. The disease was previously called dementia pugilistica (DP), i.e. "punch-drunk" as it was initially found in those with a history of boxing. CTE has now been found in the brains of professional athletes including NFL athletes who play football, athletes prone to head injury including those that play ice hockey, rugby, skiing, skateboarding, stunt performing, bull riding, rodeo, and all other contact sports where participants experience repeated brain trauma. Individuals with CTE show many signs of dementia such as memory loss, aggression, confusion, and depression, which may appear years or many decades after the trauma. In September 2015, researchers with the Department of Veterans Affairs and Boston University announced they had identified CTE in 96% of NFL football players that they had examined and in 79% of all football players (Jason Breslow, New; 87 *deceased NFL players test positive for brain disease*. Frontline Jan. 9, 2016).

The neuropathology under a microscope is clear—there is primarily an accumulation of "tangles" that consist of tau protein, similar to the "tangles" seen in the brains of Alzheimer's disease patients. There is also some beta-amyloid protein deposition (i.e. "plaques"), but this is usually uncommon and less of a feature then the "tangle" accumulation in brain. These findings suggest that blows to the head can lead to near immediate brain "tangle" accumulation that then leads to dementia-like symptoms including memory loss and cognitive decline. Identification of a nutraceutical that can help in the reduction and/or clearance of brain "tangles" would be an extraordinary supplement to take every day by all kinds of athletes, NFL players, the military and its soldiers.

DISCLOSURES

An object of the present invention is to provide the combination of plant extracts from *Uncaria tomentosa* and an oolong tea extract for the development of a cognition and memory supplement, to prevent, reduce and/or clear brain "plaques and tangles" in humans. This invention is predicated on the surprising discovery that various plant extracts, even from the same plant source have differing effectiveness for dissolving plaques and tangles, and that oolong tea extract, in particular LOTE, in combination with *Uncaria tomentosa* extract has a surprising and unexpected activity compared other plant extracts or with each extract alone.

Another object of the present invention is to provide the combination of plant extracts from *Uncaria tomentosa* and an oolong tea extract to produce a pet food supplement for aged dogs that reduce brain amyloid "plaques" and improve cognition, memory, short-term memory, focus and concentration.

Another object of the present invention is to provide the combination of plant extracts from *Uncaria tomentosa* and an oolong tea extract to produce a pet food supplement for aged cats that reduce brain amyloid "plaques" and improve cognition, memory, short-term memory, focus and concentration.

Although some health care providers have suggested that *Uncaria tomentosa* may be used to treat a variety of ailments, nowhere has there been any use, or suggestion of use, of this compound for the treatment of tau fibril formation, deposition, accumulation and/or persistence, such as that which occurs in the tauopathies. Furthermore, nowhere is it suggested that certain other compounds might have synergistic or supplemental efficacy in combination with *Uncaria tomentosa* in treating tauopathies to prevent and/or treat, for example, traumatic brain injury (TBI), concussions (as observed in most athletes and the military/soldiers), post-traumatic stress disorders, head trauma, blows to the head (either single or repeated), and chronic traumatic encephalopathy (CTE).

Another object of the present invention is to provide the combination of plant extracts from *Uncaria tomentosa* and an oolong tea extract to produce an effective preventer and/or reducer of brain "tangles," such as those found in people with traumatic brain injury (TBI), concussions (as observed in most athletes and the military/soldiers), post-traumatic stress disorders, head trauma, blows to the head (either single or repeated), and chronic traumatic encephalopathy (CTE).

The present invention clearly demonstrates the effectiveness of plant extracts of *Uncaria tomentosa* (cat's claw) in specific combination with an Oolong tea plant extract for 1) inhibition of tau fibril formation (important for patients in early- to mid-stage tauopathy), 2) inhibition of tau fibril growth (important for patients in early- to mid-stage tauopathy), and 3) causing the dissolution/disruption of preformed tau fibrils (important for late-stage tauopathy).

An object of the present invention is to use the inner bark and/or roots from *Uncaria tomentosa* (also referred to as Una de Gato or Cat's claw) for the treatment/inhibition of tau deposition, accumulation and/or persistence in tauopathies, in conjunction with an oolong tea extract, disclosed below, to achieve a beneficial therapeutic effect. *Uncaria tomentosa* or Cat's claw is also referred to as, but not limited to, Paraguayo, Garabato, Garbato casha, Tambor huasca, Una de gavilan, Hawk's claw, Nail of Cat, and Nail of Cat Schuler.

Another object of the present invention is to provide the use of *Uncaria tomentosa* with an oolong tea extract (regardless of commercial source and regardless of final form for consumption by humans, i.e. pills, tablets, caplets, soft and hard gelatin capsules, lozenges, sachets, cachets, vegicaps, liquid drops, elixirs, suspensions, emulsions, solutions, syrups, tea bags, aerosols (as a solid or in a liquid medium), suppositories, sterile injectable solutions, sterile packaged powders, bark bundles and/or bark powder) for inhibition of tau fibril formation, deposition, accumulation, and/or persistence, regardless of its clinical setting.

These and such other objects of the invention as will become evident from the disclosure below are met by the invention disclosed herein.

APPLICATIONS

Application of the invention provides for use of plant extracts from *Uncaria tomentosa* and a specific oolong tea extract to benefits aged dogs and cats, who develop brain "plaques" (and to a lesser extent, "tangles"), and have dementia, as defined in Canine Cognitive Dysfunction (CCD).

We have earlier discovered and disclosed a naturally occurring plant product, the inner bark and/or roots from the plant *Uncaria tomentosa*, or Cat's Claw, that we call PTI-00703®, in WIPO International publication number WO98/51302 entitled 'Composition and Methods for Treating Alzheimer's Disease and other Amyloidoses' dated Nov. 19, 1998, which is incorporated herein by reference in its entirety. As disclosed therein, this plant compound alone has surprising efficacy in disrupting and/or dissolving amyloid deposits and other accumulations, and is believed to be a potent inhibitor of amyloid formation in Alzheimer's disease. Type II Diabetes, and other amyloidosis.

However, our data now demonstrates that the formulation of PTI-00703® with a specific oolong tea extract (referred to as 'LOTE') disclosed herein has surprising and hitherto unsuspected potent efficacy in treating Tauopathies and diseases in which "tangles" are found in the brain (such as in TBI, CTE in humans with concussions, head injury and/or head, trauma), and diseases that contain an overabundance of "plaques in brain" such as in aged dogs and cats (in Canine Cognitive Dysfunction).

The invention relates to the use of mixed compositions including one or more of the following: oolong tea extract and *Uncaria tomentosa* extract PTI-00703® referred to as '703' or 'PTI-703' for the therapeutic intervention of amyloidosis. Use of a mixed composition of an oolong tea extract, and/or PTI-00703®, contained within different commercial preparations show unexpected effects on the inhibition of amyloid fibril formation and disaggregation of amyloid fibrils.

Application of the invention to these needs is especially beneficial in that the invention is the only system that effectively provides for use of extracts from the inner bark and root parts of *Uncaria tomentosa*, together with an oolong tea extract, to benefit human patients with Tauopathies, amyloid diseases, "plaques and/or tangles" in the brain, and those with traumatic brain injury (TBI), concussions (as observed in most athletes and the military/soldiers), post-traumatic stress disorders, head trauma, blows to the head (either single or repeated), and chronic traumatic encephalopathy (CTE).

Application of the invention to these needs is especially beneficial in that the invention is the only system that effectively provides for use of extracts from the inner bark and root parts of *Uncaria tomentosa*, together with an Oolong tea extract, to benefit human patients with tauopathies, due to the newly discovered ability of *Uncaria tomentosa* in combination with an oolong tea extract, to effectively inhibit tau fibril formation, inhibit tau fibril growth, inhibit fibrillar tau-proteoglycan interactions, fibrillar tau-glycosaminoglycan interactions, and cause dissolution and/or disruption of preformed tau fibrils.

Over 25 extracts of teas, along with extracts of coffee and yerba mate, were screened for amyloid fibril aggregation inhibition and disaggregation in vitro using a variety of assays. One lead oolong tea extract was selected and tested in combination with PTI-00703®. It was found that the combination of this specific lead oolong tea extract (LOTE) and PTI-00703® inhibited amyloid fibril formation more than the tea extract or PTI-00703® alone, and the combination of LOTE and PTI-00703® also had the ability to rapidly disaggregate (within 15 minutes) preformed amyloid fibrils.

The invention also relates to the use of mixed compositions including one or more of the following: oolong tea extract and *Uncaria tomentosa* extract PTI-00703 referred to as '703' or 'PTI-703' for the therapeutic intervention of tauopathies. Use of a mixed composition of oolong tea extract, and/or PTI-00703, contained within different commercial preparations show unexpected effects on the inhibition of tau fibril formation and disaggregation of tau fibrils.

Over 25 extracts of teas along with extracts of coffee and yerba mate were screened for tau fibril aggregation inhibition and disaggregation in vitro. One lead oolong tea extract was selected and tested in combination with PTI-00703®. It was found that the combination of this specific lead oolong tea extract (LOTE) and PTI-00703® inhibited tau fibril formation more than the tea extract or PTI-00703® alone, and also has the ability to rapidly disaggregate preformed tau fibrils.

It was also found that the combination of this specific lead oolong tea extract (LOTE) and PTI-00703® inhibited beta-amyloid protein fibril formation more than the tea extract or PTI-00703® alone, and also has the ability to rapidly disaggregate preformed amyloid fibrils.

A preferred pharmacological agent preferably has a therapeutically effective amount of *Uncaria tomentosa* in a dosage in the range of from about 10 to about 1,000 mg/kg of body weight of the patient, and more preferably in the range of from about 10 to about 100 mg/kg of body weight of the patient.

The compositions preferably have a therapeutically effective amount of the mixed composition lead oolong tea extract (LOTE) and PTI-00703®, in a dosage in the range of from about 0.1 to about 500 mg/kg of body weight of the patient, and more preferably in the range from about 1.0 to about 100 mg/kg of body weight of the patient.

Preferred pharmaceutical agents may also have a pharmaceutically acceptable carrier, diluent or excipient. The pharmaceutical agent preferably has a fibril inhibitory activity or efficacy greater than 50%.

The plant matter is preferably comprised of commercially obtained pills, tablets, caplets, soft and hard gelatin capsules, lozenges, sachets, cachets, vegicaps, liquid drops, elixirs, suspensions, emulsions, solutions, syrups, tea bags, aerosols (as a solid or in a liquid medium), suppositories, sterile injectable solutions, sterile packaged powders, bark bundles and/or bark powder, which contain *Uncaria tomentosa*, extracts or derivatives thereof (and may be taken from commercially available gelatin-coated capsules which contain dried powder of *Uncaria tomentosa*, extracts or derivatives thereof), in combination with a specific oolong tea extract.

An object of the present invention is to use the inner bark and/or roots from *Uncaria tomentosa* (also referred to as Una de Gato or Cat's claw) for the treatment/inhibition of amyloid deposition, accumulation and/or persistence in amyloidosis, in conjunction with an oolong tea extract, disclosed below, to achieve a beneficial therapeutic effect. *Uncaria tomentosa* or cat's claw is also referred to as, but not limited to, Paraguiayo, Garabato, Garbato casha, Tambor huasca, Una de gavilan, Hawk's claw, Nail of Cat, and Nail of Cat Schuler.

Another object of the present invention is to provide the use of *Uncaria tomentosa* with an oolong tea extract (regardless of commercial source and regardless of final form for consumption by humans, i.e. pills, tablets, caplets, soft and hard gelatin capsules, lozenges, sachets, cachets, vegicaps, liquid drops, elixirs suspensions, emulsions, solutions, syrups, tea bags, beverage preparations, aerosols, as a solid or in a liquid medium, suppositories, sterile injectable solutions, sterile packaged powders, bark bundles and/or bark powder, for inhibition of amyloid fibril formation, deposition, accumulation and/or persistence, regardless of its clinical setting.

Application of the invention to these needs is especially beneficial in that the invention is the only system that effectively provides the use of extracts from the inner bark and root parts of *Uncaria tomentosa*, together with a specific Oolong tea extract, to benefit human patients with amyloidosis, and aged mammals (such as dogs and cats that develop amyloid "plaques" in the brain as they age), due to the newly discovered ability of *Uncaria tomentosa* in combination with an Oolong tea extract, to most remarkably and effectively inhibit amyloid fibril formation, inhibit amyloid fibril growth, and cause dissolution and/or disruption of preformed amyloid fibrils.

A method is also disclosed for treating tauopathy in a patient, comprising the step of administering to the patient a therapeutically effective amount of plant matter from a plant of the genus *Uncaria*, species *tomentosa*, in combination with an Oolong tea extract. The plant matter is preferably administered orally such as in oral capsules, beverage preparations, or any other method, or by aerosol spray or in a parenterally injectable or infusible form.

BRIEF DESCRIPTION OF THE DRAWINGS

This paragraph intentionally left blank.

DETAILED DESCRIPTION

A "therapeutically effective amount" in general means the amount that, when administered to a subject or animal for treating a disease, is sufficient to affect the desired degree of treatment for the disease. A "therapeutically effective amount" or a "therapeutically effective dosage" preferably inhibits, reduces, disrupts, disassembles tau fibril formation, deposition, accumulation and/or persistence, or treats a disease associated with these conditions, such as a tauopathy, by at least 20%, more preferably by at least 40%, even more preferably by at least 60%, and still more preferably by at least 80%, relative to an untreated subject. Effective amounts of a compound of this invention or composition thereof for treatment of a mammalian subject are about 0.1 to about 1000 mg/Kg of body weight of the subject/day, such as from about 1 to about 100 mg/Kg/day, especially from about 10 to about 100 mg/Kg/day. A broad range of disclosed composition dosages are believed to be both safe and effective.

"Amyloid diseases" or "amyloidosis" suitable for treatment with the compositions of this inventions are diseases associated with the formation, deposition, accumulation, and/or persistence of amyloid fibrils, especially the fibrils of an amyloid protein selected from the group consisting of beta-amyloid protein or Aβ, AA amyloid, AL amyloid, IAPP amyloid, PrP amyloid, α2-microglobilin amyloid, transthyretin, prealbumin, and procalcitonin, especially Aβ and IAPP amyloid, Suitable such diseases include Alzheimer's disease, Down's syndrome, Mild cognitive impairment (MCI), Cognitive Canine Dysfunction (CDD), traumatic brain injury (TBI), chronic traumatic encephalopathy (CTE), concussions, hear trauma, single- and multiple blows to the head, post-traumatic stress disorders, dementia pugilistica, multiple system atrophy, inclusion body myositosis, hereditary cerebral hemorrhage with amyloidosis of the Dutch type, Niewman-Pick disease type C, cerebral β-amyloid angiopathy, dementia associated with cortical basal degeneration, the amyloidosis of type 2 diabetes, the amyloidosis of chronic inflammation, the amyloidosis of malignancy and Familial Mediterranean Fever, the amyloidosis of multiple myeloma and B-cell dyscrasias, the amyloidosis of prion diseases, Creutzfeldt-Jakob disease, Gertsmann-Straussler syndrome, kuru, scrapie, the amyloidosis associated with carpal tunnel syndrome, senile cardiac amyloidosis, familial amyloidotic polyneuropathy, and the amyloidosis associated with endocrine tumors.

"Fibrillogenesis" refers to the formation, deposition, accumulation and/or persistence of tau fibrils, filaments, inclusions, deposits, inclusions, or the like.

"Inhibition of fibrillogenesis" refers to the inhibition of formation, deposition, accumulation and/or persistence of such amyloid "plaque" or tau "tangle" fibril-like deposits.

"Disruption of fibrils or fibrillogenesis" refers to the disruption of preformed beta-amyloid or tau fibrils that usually exist in a pre-dominant β-sheet, secondary structure. Such disruption by compounds of the invention may involve marked reduction or disassembly of beta-amyloid or tau fibrils as assessed by various methods such as circular dichroism spectroscopy, Thioflavin S fluorometry, SDS-PAGE/Western blotting, or negative stain electron microscopy, as demonstrated by the Examples presented in this application.

"Mammal" includes both humans and non-human mammals, such as companion animals (dogs, cats and the like), laboratory animals (such as mice, rats, guinea pigs, and the like) and farm animals (cattle, horses, sheep, goats, swine, and the like).

"Plaques" refer to the meatball looking "amyloid deposits" consisting of beta-amyloid protein or Aβ found in various regions of brain (including hippocampus, cerebral cortex, frontal cortex etc.) that is a pathological hallmark of brain aging, mild-cognitive impairment (MCI), Alzheimer's disease, and is found in aging mammals such as dogs, cats (referred to as Cognitive Canine Dysfunction or CDD), monkeys, polar bears, horses and the like. Accumulation of amyloid "plaques" in brain is believed to lead to neurodegeneration, loss of synapses and connections between neurons, cognitive decline, memory decline and loss, and loss of focus and concentration.

"Tangles" refer to the "dried-up" spaghetti looking "tangle-deposits" consisting of tau protein found in various regions of brain (including hippocampus, cerebral cortex, frontal cortex etc.) that is a pathological hallmark of brain aging, mild-cognitive impairment, Alzheimer's disease, concussions, traumatic brain injury (TBI), single and repeated blows to the head, post-traumatic stress disorders, chronic traumatic encephalopathy (CTE) and the like.

"Tauopathies" suitable for treatment with the compounds of this invention are also diseases associated with the formation, deposition, accumulation, or persistence of tau fibrils. Suitable diseases include Alzheimer's disease, frontotemporal lobar degeneration with tau inclusions (FTLD-tau) such as Pick's disease, progressive supranuclear palsy, and corticobasal degeneration, agyrophillic grain disease, some prion diseases, amyotrophic lateral sclerosis/parkinsonism-dementia complex of Guam (also called Lytico Bodig disease), dementia pugilistica, chronic traumatic encephalopathy, Parkinson's disease and particularly some genetic forms of Parkinson's disease, tangle-predominant dementia (with neurofibrillary tangles similar to Alzheimer's disease, but without amyloid plaques).

Tau fibrils is a generic term referring to a group of diverse, but specific intracellular or extracellular protein deposits which all have common morphological properties, staining characteristics, and x-ray diffraction spectra.

"Treating" or "treatment" of a disease includes preventing the disease from occurring in a mammal that may be predisposed to the disease but does not yet experience or exhibit symptoms of the disease (prophylactic treatment). Treatment can also mean inhibiting the disease (slowing or arresting its development), providing relief from the symptoms or side-effects of the disease (including palliative treatment), and relieving the disease (causing regression of the disease), such as by disruption of preformed tau fibrils. Treatment does not need be absolute. One such preventive treatment may be use of the disclosed compounds for the treatment of Mild Cognitive impairment (MCI).

The plant *Uncaria tomentosa*, also known as "Uña de Gato" (in Spanish) or "Cat's claw" (in English) refers to a woody vine which grows within the Peruvian Amazon rain forest. This slow-growing vine takes 20 years to reach maturity, and can grow over 100 feet in length as it attaches and wraps itself around the native trees. It is found abundantly in the foothills, at elevations of two to eight thousand feet. The vine is referred to as "cat's claw" because of its distinctive curved claw-like thorns that prefect from the base of its leaves. *Uncaria tomentosa* is expected to have immune-supporting, anti-inflammatory, anti-viral, anti-mutagemic and antioxidant properties. The anti-inflammatory properties, for example, are expected to be beneficial for the treatment of arthritis, rheumatism, bursitis and gout. Without being bound by theory, it is believed that is beneficial effects in treating arthritis pain can be due, in part, to its ability to cleanse the digestive tract and aid in removing toxins from the body. Furthermore, *Uncaria tomentosa* or cat's claw is expected to alleviate pain, and is expected to be helpful in reducing pain associated with, for example, chemotherapy, radiation treatment and AZT use.

*Uncaria tomentosa* or cat's claw is also expected to be useful in stopping viral infections in stopping viral infections in the early stages, fighting opportunistic infections in AIDs patients and decreasing the viable size of some skin tumors and cysts. *Uncaria tomentosa* can also be used to treat a variety of ailments, including cancer, AIDs, Crohn's disease, respiratory infections, allergies, herpes, prostrate problems, lupus, Epstein Barr virus, chronic fatigue syndrome, and a variety of stomach and bowl disorders.

For additional and further information and background on *Uncaria tomentosa*, the reader is also referred to the inventor's WIPO International publication number W098/51302, which is incorporated herein by reference in its entirety.

Further Aspects and Utilizations of the Invention

Another embodiment of the present invention is to formulate, prior to administration in a patient, a pharmaceutical blend comprising *Uncaria tomentosa* and an oolong tea extract in one or more pharmaceutical acceptable carriers, diluents or excipients.

In another embodiment *Uncaria tomentosa* obtained commercially in any form could be further modulated using suitable carriers, excipients and diluents including lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed response of the active ingredient after administration to the patient. The compositions are preferably formulated in a unit dosage form, each dosage containing from about 1 to about 10,000 mg of *Uncaria tomentosa* (or its active ingredients), more usually about 500 to about 2,000 mg of *Uncaria tomentosa* (or its active ingredients).

However, it will be understood that the therapeutic dosage administered will be determined by the physician in the light of the relevant circumstances including the clinical condition to be treated, the organ or tissues affected or suspected to be affected with tau fibril accumulation, and the chosen route of administration. Therefore, the above dosage ranges are not intended to limit the scope of the invention in any way.

The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

Use of extracts from the inner bark and root parts of *Uncaria tomentosa*, and its blends benefit human patients with tauopathies due to the newly discovered ability of *Uncaria tomentosa* in combination with an Oolong tea extract to inhibit tau fibril formation, inhibit tau fibril growth, inhibit tau fibril-proteoglycan interactions, inhibit tau fibril-glycosaminoglycan interactions, and cause dissolution and/or disruption of preformed tau fibrils.

Compositions and Administration

In general, isolated, and/or purified *Uncaria tomentosa* and oolong tea plant extracts are administered in therapeutically effective amounts by any of the usual modes known in the art, either singly or in combination with at least one of the extracts of the disclosure. Administration will be by one of the following routes: oral, topical, and synthetic (e.g. transdermal, intranasal or by suppository), or parenteral (e.g. intramuscular, subcutaneous, or intravenous injection). Compositions can take the form of tablets, pills, capsules, semisolids, powders, sustained release formulations, solutions, suspensions, elixers, aerosols, or any other appropriate compositions, and comprise at least one pharmaceutical acceptable excipient. Suitable excipients are well known to persons of ordinary skill in the art, and they, and the methods of formulating the compositions, can be found in standard references as Alfonso A R: Remington's Pharmaceutical Sciences, 17th ed., Mack Publishing Company, Easton, Pa., 1985. Suitable liquid carriers, especially for injectable solutions, include water, aqueous saline solution, aqueous dextrose solution, and glycols.

In particular, the compound(s) can be administered orally, for example, as tablets, trouches, lozenges, aqueous or oily suspensions, dispersible powders or granules, emulsions, hard or soft capsules, syrups or elixers. In one embodiment, only one such compound is administered in any particular dosage form. Compositions intended for oral use can be prepared to any method known in the art for the manufacture of nutraceutical compositions and such compositions can contain one or more agents selected from the group consisting of sweetening agents, flavoring agents, coloring agents and preserving agents in order to provide nutraceutically elegant and palatable preparations.

Tablets contain the plant extracts in admixture with non-toxic pharmaceutically acceptable excipients that are suitable for the manufacture of tablets. These excipients include, for example, inert diluents, such as calcium carbonate, sodium carbonate, lactose, calcium phosphate or sodium phosphate; granulating and disintegrating agents, for example, maize starch or alginic acid; binding agents, for example, maize starch, gelatin or acacia; and lubricating agents, for example magnesium stearate or stearic acid or talc. The tablets can be uncoated or they can be coated by known techniques to delay disintegration and absorption in the gastrointestinal tract and thereby provide a sustained action over a longer period. For example, a time delay material such as glycerol monostearate or glycerol distearate can be employed. Formulations for oral use can also be prepared as hard gelatin capsules wherein the compounds are mixed with an inert solid diluent, for example, calcium carbonate, calcium phosphate or kaolin, or as soft gelatin capsules, wherein the active ingredient is mixed with water or an oil medium, for example, peanut oil, liquid paraffin or olive oil.

Aqueous suspensions contain the compound in admixture with excipients suitable for the manufacture of aqueous suspensions. Such excipients include, for example, suspending agents, for example, sodium carboxymethylcellulose, methylcellulose, hydroxypropylmethyl cellulose, sodium alginate, polyvinylpyrrolidone, gum tragacanth and gum acacia; and dispersing and wetting agents that are naturally occurring phosphatides, for example lecithin, or condensation products of an alkylene oxide with fatty acids; for example polyoxyethylene stearate, or condensation products of ethylene oxide with long chain aliphatic alcohols, for example heptadecaethyleneoxycetanol, or condensation products of ethylene oxide with partial esters derived from fatty acids such as hexitol, for example polyoxyethylene sorbitol monooleate, or condensation products of ethylene oxide with partial esters from fatty acids and a hexitol annyhydride, for example polyethylene sorbitan monooleate. The aqueous suspensions can also contain one or more preservatives, for example ethyl or n-propyl p-hydroxybenzoate, one or more coloring agents, one or more flavoring agents, and/or one or more sweetening agents, such as sucrose or saccharin.

Oily suspensions can be formulated by suspending the extracts in a vegetable oil, for example arachs oil, olive oil, sesame oil, or coconut oil, or in a mineral oil such as liquid paraffin. The oily suspensions can contain a thickening agent for example beeswax, hand paraffin or cetyl alcohol. Sweetening agents, such as those set forth below, and flavoring agents can be added to provide a palatable oral preparation. These compositions can be preserved by the addition of an antioxidant such as ascorbic acid.

Dispersible powders and granules suitable for preparation of an aqueous suspension by the addition of water provide the active ingredients in admixture with a dispersing or wetting agent, a suspending agent and one or more preservatives. Suitable dispersing or wetting agents and suspending agents are exemplified by those already described above. Additional excipients, for example sweetening, flavoring and agents, can also be present.

The plant extracts can also be in the form of oil-in-water emulsions. The oily phase of a vegetable oil, for example, olive oil or arachis oils, or a mineral oil, for example liquid paraffin, or mixtures thereof. Suitable emulsifying agents can be naturally-occurring gums, for example gum acacia or gum tragacanth, naturally occurring phosphatides, for example soy bean, lecithin, and esters or partial esters derived from fatty acids and hexitol anhydrides, for example sorbitan esters with ethylene oxide, for example polyoxyethylene sorbitan monooleate, and condensation products of the said partial esters with ethylene oxide, for example polyethylene sorbitan monooleate. The emulsion can also contain sweetening and flavoring agents. Syrups and elixers can be formulated with sweetening agents, for example, glycerol, sorbitol or sucrose. Such formulations can also contain a demulcent, a preservative and flavoring and coloring agents.

The following non-limiting Examples are given by way of illustration only and are not considered a limitation of this disclosure, many apparent variations of which are possible without departing from the spirit or scope thereof.

EXAMPLES

Composition Preparation

For these studies, commercially available tea leaves or extracts were obtained from various vendors. To make tea extracts from tea leaves, 2 g of tea leaves were extracted into 100° C. deionized water for 20 min with occasional mixing. Tea extracts were filtered through a >10 μm cut-off fitter to remove large particulates. Extracts were snap frozen in dry ice/ethanol then lyophilized to obtain a dried, concentrated powder. Dried powder was weighed and resuspended in DMSO to make concentrated 100 mg/ml stock solutions. Stock solutions were diluted into aggregation reactions such that DMSO concentration was less than 0.28% in the final reaction.

LOTE was prepared from oolong tea (AuNutra Industries Inc., Chino, Calif.). PTI-00703® is a powder extract made from water extraction of the inner bark of Peruvian *Uncaria tomentosa* (RFI Ingredients, Blauvelt, N.Y.). Methods for preparing PTI-00703® have been described, for example in WIPO International Pub, No. W098/51302. Ethanol extracts of oolong tea and/or *Uncaria tomentosa* are within the scope of the current invention.

Example 1: Compositions of this Invention are Potent Disrupters/Inhibitors of Alzheimer's Aβ Fibrils or Aggregates The compositions were found to be potent disrupter/inhibitors of Aβ protein fibrils or aggregates. In a set of studies, the efficacy of the compositions to cause disassembly/disruption/disaggregation of pre-formed amyloid fibrils of Alzheimer s disease (i.e. consisting of Aβ 1-42 or Aβ 1-40) was analyzed.

Part A: Thioflavin T Fluorometry

In this study, Thioflavin T fluorometry was used to determine the effects of the compositions. Thioflavin T specifically binds to fibrillary amyloid, and this binding produces a fluorescence enhancement at 485 nm that is directly proportional to the amount of amyloid fibrils formed. The higher the fluorescence, the greater the amount of amyloid fibrils formed (Nakai et al., Lab. Invest, 65:104-110, 1991; Levine III, Protein Sci. 2:404-410, 1993; Amyloid: Int. J. Exp. Clin. Invest. 2:1-6, 1995).

In this study, 40 μl of a 1 mg/ml solution (in distilled water) or pre-fibrillized human Aβ 1-42 (rPeptide) was incubated at 37° C. for 3 days either alone (control), or in the presence of LOTE+PTI-00703® (at test composition:Aβ weight ratios of 1:1 and 1:0.1) (referred to as "Cognitive Clarity™"). The final concentration of Aβ in the reaction was 0.4 mg/ml (88 μM) in phosphate-buffered saline (PBS), pH 7.4+0.02% sodium azide in 100 μl final volume. Following 3-days of co-incubation, 12.5 μl of each incubation mixture was transferred into a 96-well microtiter plate containing 37.5 μl of PBS and 200 μl of a Thioflavin T solution (i.e. 125 μM Thioflavin T in 62.5 mM phosphate buffer, pH 6.8). The emission fluorescence was read at 485 nm (444 nm excitation wavelength) using an ELISA plate fluorometer after subtraction with buffer alone or composition alone, as blank.

Figure 1:
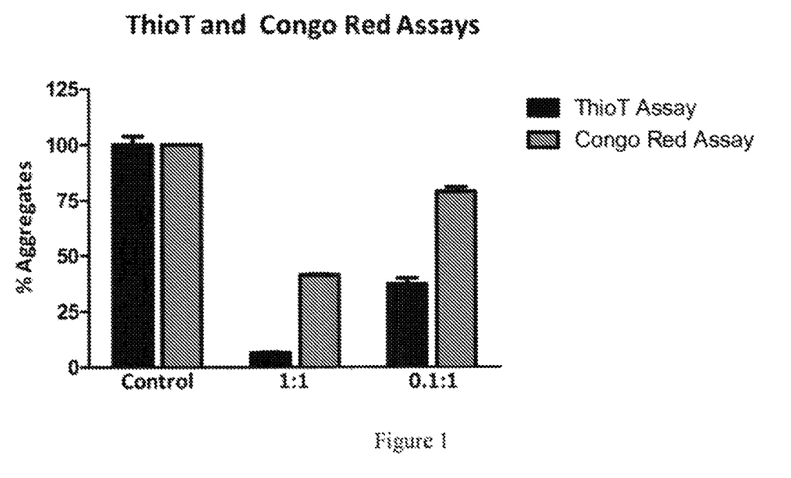
FIG. 1 A graph of Aβ 1-42 aggregation measured by Thioflavin T fluorometry and Congo red binding after incubation with lead Oolong tea extract (LOTE) and PTI-00703®

The results of the 3-day incubations are presented in FIG. 1. Incubation of Aβ 1-42 with "Cognitive Clarity" (i.e. combination of LOTE+PTI-00703®) caused a dose-dependent disruption disassembly/disaggregation of preformed Aβ 1-42 fibrils. At a test composition. Aβ weight ratio of 0.1:1 LOTE+PTI-00703 inhibited fibrils 62.8%. At equal weight equivalents (test composition:Aβ weight radio of 1:1) there was a 93.6% inhibition of Thioflavin T fluorescence. This study indicated that this unique combination is a potent disruptor/inhibitor of Alzheimer's disease type Aβ fibrils, and exerts its effect in a dose-dependent manner.

Part B: Congo Red

In the Congo red binding assay the ability of a test composition to alter β-amyloid binding to Congo red is quantified. In this assay, Aβ 1-42 (as prepared for the Thioflavin T assay) was incubated for 3 days either alone (control), or with increasing amounts of test compositions and then vacuum filtered through a 0.2 μm filter. The amount of Aβ1-42 retained in the filter was then quantitated following staining of the filter with Congo red (125 μM Congo red, 100 mM Tris, 50 mM NaCl, pH 7). After appropriate washing of the filter, any lowering of the Congo red color on the filter in the presence of the test composition (compared to the Congo red staining of the amyloid protein in the absence of the test composition) was indicative of the test composition's ability to diminish/alter the amount of aggregated and congophilic Aβ.

In one study, the ability of Aβ fibrils to bind Congo red in the absence or presence of increasing amounts of LOTE+ PTI-007003® (at test composition:Aβ weight ratios of 1:1, and 0.1:1) was determined. The results of 3-day incubations are presented in FIG. 1 LOTE+PTI-00703® caused a dose-dependent inhibition of Aβ binding to Congo red. At a test composition:Aβ weight ratio of 0.1:1, LOTE+PTI-00703® inhibited Congo red binding 20.9% ($p<0.001$). At equal weight equivalents (test composition:Aβ weight ratio of 1:1) there was a 58.6% ($p<0.001$) inhibition of Congo red binding.

Similar to the results for the Congo red binding assay, this study also indicated that this combination of a specific lead oolong tea extract (LOTE) and PTI-00703® are potent disrupters/inhibitors of Aβ fibrils as assessed by a Thioflavin T fluorometry assay, and exerted its effects in a dose-dependent manner (FIG. 1). The combination of LOTE+ PTI-00703® caused a dose dependent reduction of Thioflavin T binding (indicating disruption/reduction of Aβ fibrils) by 70% ($p<0.001$) at a test composition:Aβ weight ratio of 0.1:1 (FIG. 1), and by 95% at a test composition:Aβ weight ratio of 1:1 (FIG. 1).

Part C: Slide-Based Congo Red Binding, Thioflavin S and Electron Microscopy

In the slide-based Congo red assay, Congo red dye is incubated with Aβ1-42, dotted on a slide and imaged under polarized light. Amyloid fibrils bound by Congo red emits a characteristic "apple-green birefringence" under polarized light. In this study, pre-fibrillarized 0.4 mg/ml Aβ1-42 (as prepared for the Thioflavin T assay) with or without test compositions was incubated for 3 days. 10 μl Congo red solution (250 mg Congo red dye (54% pure; Sigma) dissolved in 1 L dH2O) was added to 10 μl of Aβ1-42–/+ test compositions and mixed by vortexing for 30 seconds. Samples were incubated 10 minutes at room temperature with Congo red solution. Samples were then centrifuged at 2000 g for 3 minutes and 10 μl of supernatant was removed. 2 μl glycerol was added to the pellet and mixed by pipetting up and down 15 times. Sample was vortexed then 10 μl of stained protein was dotted onto 18-well 5 MM HTC® autoclavable blue slides. Samples were covered with small circular coverslips and then immediately imaged under polarized light. Images were captured with a Zeiss Axioscope 2 Plus microscope with HBO 100 illuminator equipped with a Q-Imaging Retiga 1300 digital camera.

Figure 2A:
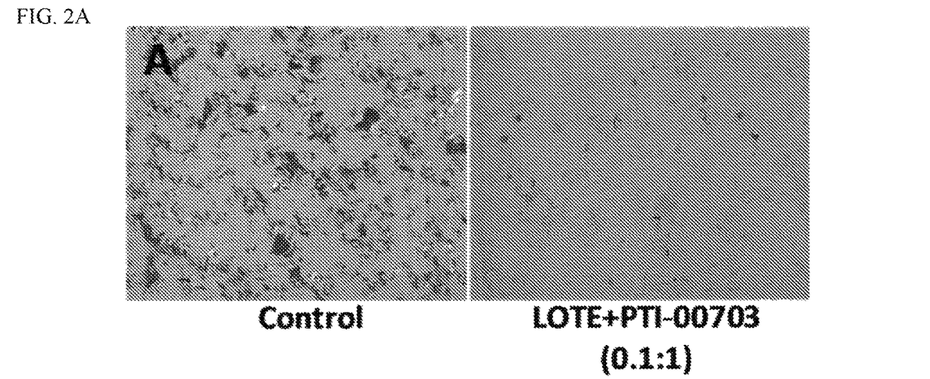
FIG. 2A-C Representative images of Congo red, Thioflavin S, and electron micrographs of Aβ fibrils+/− LOTE and PTI-00703®

In FIG. 2A (left panel), a representative image shows that untreated Aβ1-42 has characteristic apple-green birefringence and abundant fibrillar protein uniformly distributed across the viewing field. In FIG. 2A (right panel) treatment with LOTE+PTI-00703 (0.1:1 weight ratio with Aβ42) resulted in substantially less Congo red stained fibrils, demonstrating that the plant extract combination can reduce and disaggregate/dissolve pre-formed Aβ 1-42 pre-formed fibrils.

Similar to Thioflavin T, Thioflavin S is a related anionic dye that binds to fibrillar amyloid proteins and can be used to detect fibrillar proteins bound to a glass microscope slide. In this study, prefibrillarized Aβ1-42 (as prepared for the Thioflavin T assay) with or without test compositions was incubated for 3 days. 4 μl of 0.4 mg/ml Aβ 1-42–/+ test compositions were dotted onto 18-well 5 MM HTC® autoclavable blue slides. Samples were allowed to air dry for 2 h. 10 μl of Thioflavin S solution (31 mg of Thioflavin S dissolved in 50 mL dH2O) was gently applied to dried protein on slides. Protein was stained for 1 minute, then Thioflavin solution was removed by pipette. 40 μl of a 70% ethanol solution was gently pipetted onto stained protein for 1 minute to rinse. This solution was gently removed by pipette. 2 μl of Vectashield (Vector) mounting media was applied to the stained protein and then covered with circular coverslips. Images were viewed under fluorescent light and images captured with a Zeiss Axioscope 2 Plus microscope with HBO 100 illuminator equipped with a Q-Imaging Retiga 1300 digital camera.

Figure 2B:
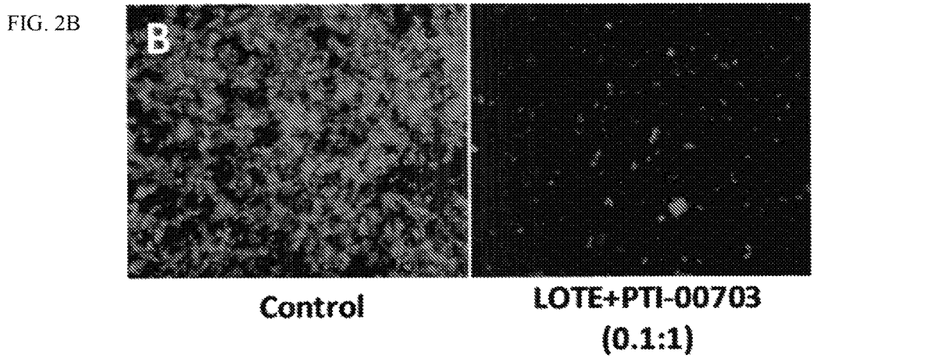

In FIG. 2B (left panel), a representative image of untreated Aβ 1-42 shows abundant Thioflavin S fluorescent fibrils uniformly distributed across the viewing field. Pre-formed Aβ 1-42 fibrils incubated with LOTE+PTI-00703® (at 0.1:1 weight ratio with Aβ1-42) for 72 hr showed a substantial reduction in fluorescent fibrils (FIG. 2B, right panel).

In FIG. 2B (right panel), representative images show that with LOTE+PTI-00703 treatment, the Thioflavin S-fluorescent fibrils disappeared.

Negative stain electron microscopy (EM) analysis was used to independently monitor the effectiveness of different compositions to disrupt pre-formed Aβ fibrils. In these experiments, pre-formed Aβ 1-42 fibrils (as prepared for the Thioflavin T assay) were incubated in the absence (control) or presence of increasing concentrations of test compositions. After the 3-day incubation, 10 μl samples were spotted onto grids, stained with 2% uranyl acetate, and visualized at 8,000× to 30,000× magnifications with a JEOL 1010 transmission electron microscope.

Figure 2C:
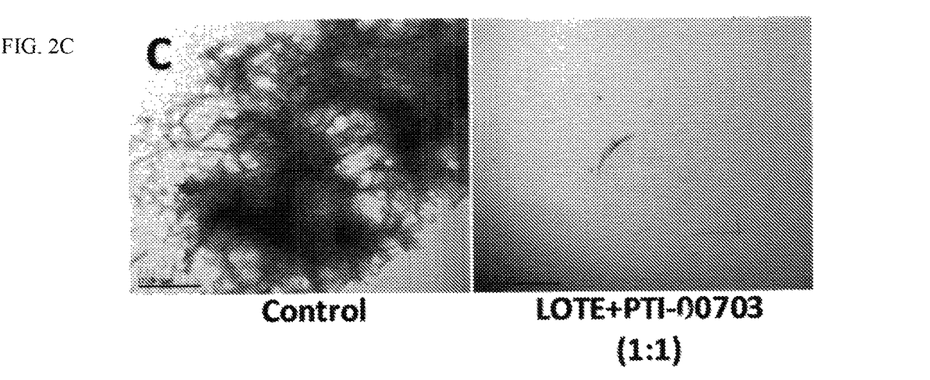

In FIG. 2C (bottom panel), EM analysis confirmed formation of Aβ fibrils in the absence of treatment (i.e. FIG. 2C, Control). Without treatment (2C, left panel), Aβ formed large clumped fibrils that uniformly covered the field. These samples were also tested by the Thioflavin T assay and confirmed to be Thioflavin T-fluorescence positive fibrils. In the presence of LOTE+PTI-00703® (FIG. 2C, right panel), the number of clumped Aβ fibrils was significantly reduced and dissolved. These results correlate well with the Thioflavin T fluorometry date that showed a reduction in Thioflavin T fluorescence with treatment and Congo red binding data that showed a reduction in Congo red binding with treatment. Using these independent methodologies, we have identified and validated the lead oolong tea extract (LOTE) in combination with PTI-00703® (i.e. LOTE+PTI-00703®) as potent Aβ disrupters/inhibitors.

Example 2: Compositions of this Invention Directly Inhibit/Disrupt the In Vitro Conversion of Aβ to β-Sheet Containing Fibril Structures Part A: Thioflavin T Fluorometry To test whether LOTE+PTI-00703® can inhibit the β-sheet formation of Aβ, the same Thioflavin T assay as described in Example 1 was utilized, but with Aβ 1-40 as a substrate instead. Similar to Aβ1-42, Aβ 1-40 forms Thioflavin T positive aggregates but requires >24 h incubation at 37° C. shaking to become fully fibrillarized. Since Aβ 1-40 is in a non-fibrillar state at the start of the assay, this protein can be aggregated in the presence of compositions to measure aggregation inhibition. Lyophilized human Aβ 1-40 (rPeptide) was dissolved to 1 mg/mL (220 µM) in dH2O. In separate test tubes, test composition stocks were prepared in PBS at various concentrations such that final reactions containing equal volumes of the test composition stocks and the Aβ solution would result in a final Aβ concentration of 0.5 mg/mL (110 µM) with test composition:Aβ weight ratios of 1:1, 0.5:1, 1:1, and 0.2:1. The reactions containing Aβ+test compositions (or Aβ+PBS as a control for Aβ aggregation) were then incubated for 2 days. The incubation mixtures were diluted 1:10 to 0.05 mg/ml. Aβ and 50 µL of each diluted incubation mixture was transferred into a 96-well microliter plate containing 200 µL of Thioflavin T solution (i.e. 125 µM Thioflavin T in 62.5 mM phosphate buffer, pH 6.8). The fluorescence was read at 485 nm (444 nm excitation wavelength) using an ELISA plate fluorometer after subtraction with PBS buffer alone or composition alone, as blank.

Figure 3:
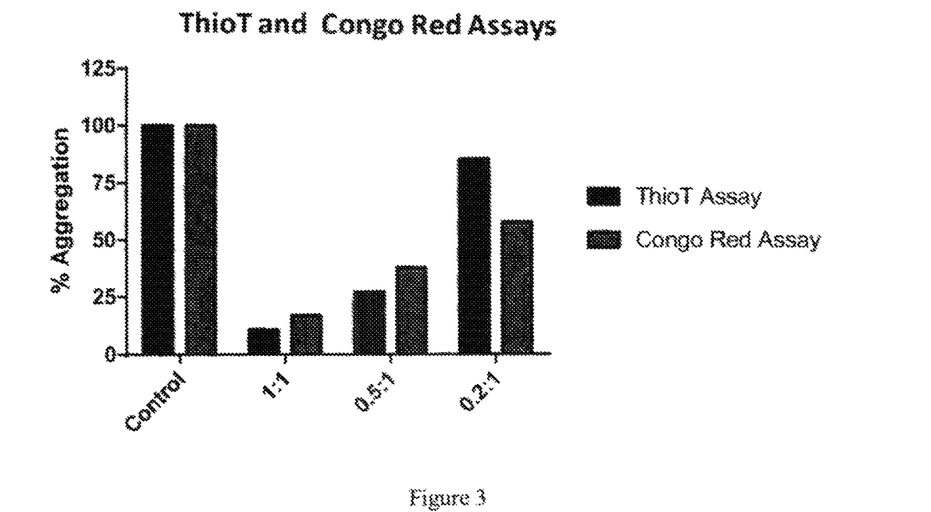
FIG. 3 A graph of Aβ 1-40 aggregation measured by Thioflavin T fluorometry and Congo red binding after incubation with LOTE and PTI-00703®

The results of this study presented in FIG. 3 indicated that LOTE+PTI-00703® of this invention interfered with Aβ aggregation as indicated by its ability to prevent the formation of fibrils as assessed by Thioflavin T fluorometry. At a test composition:Aβ weight ratio of 0.2:1 LOTE+PTI-00703® inhibited fibrils by 14.1% and at 0.5:1 LOTE+PTI-00703® inhibited fibrils at 73% (p<0.001). At equal weight equivalents (test composition:Aβ weight ratio of 1:1) there was an 89.3% inhibition (p<0.001) of Thioflavin T fluorescence. This study indicated that LOTE+PTI-00703® is a potent inhibitor of β-sheet rich-Aβ fibril formation as assessed by Thioflavin T fluorometry, and this combination exerts its effect in a dose-dependent manner.

Part B: Congo Red

To test whether LOTE+PTI-00703® can inhibit β-sheet formation of Aβ the same Congo red assay as described in Example 1 was utilized, but with Aβ 1-40 as a substrate instead. In this assay, Aβ 1-40 (as prepared for the Thio T assay) and test compositions were incubated for 2 days and then vacuum filtered through a 0.2 µm filter. The amount of Aβ 1-40 retained in the filter was then quantitated following staining of the filter with Congo red (125 µM Congo red, 100 mM Tris, 50 mM NaCl, pH 7). After appropriate washing of the filter, any lowering of the Congo red color on the filter in the presence of the test composition (compared to the Congo red staining of the amyloid protein in the absence of the test composition) was indicative of the test composition's ability to diminish/alter the amount of aggregated and congophilic Aβ.

In one study, the ability of Aβ fibrils to bind Congo red in the absence or presence of increasing amounts of LOTE+ PTI-00703® (at test composition:Aβ weight ratios of 1:1, 0.5:1, and 0.2:1) was determined. The results of 2-day incubations are presented in FIG. 3. LOTE+PTI-00703® caused a dose-dependent inhibition of Aβ binding to Congo red. At a test composition:Aβ weight ratio of 0.2:1 LOTE+ PTI-00703 inhibited Congo red binding 41.7% and 0.5:1 LOTE+PTI-00703® inhibited Congo Red binding 62.5% (p<0.001). At equal weight equivalents (test composition: Aβ weight ratio of 1:1) there was an 83.3% inhibition (p<0.001) of Congo red binding. Similar to the results for the Thioflavin T fluorometry assay, this study also indicated that LOTE+PTI-00703® is a potent inhibitor of Aβ fibrils as assessed by Aβ fibril binding to Congo red, and exerts its effect in a dose-dependent manner.

Part C: CD Spectroscopy

CD spectroscopy was performed to determine LOTE+ PTI-00703®'s potency to inhibit formation of Aβ 1-40 β-sheet secondary structure under aggregation-prone conditions. Since β-sheet structure is characteristic of Aβ fibrils, monitoring secondary structure of protein can provide additional proof of a compositions' effectiveness at inhibiting aggregation. CD spectra of Aβ 1-40 samples with increasing –/+ concentrations of compositions were analyzed at 25° C. on a JASCO Model J-810 Spectropolarimeter. CD spectroscopy and ThioT assays were analyzed in parallel from the same sample preparation in order to correlate the results from two independent assays.

Figure 4:
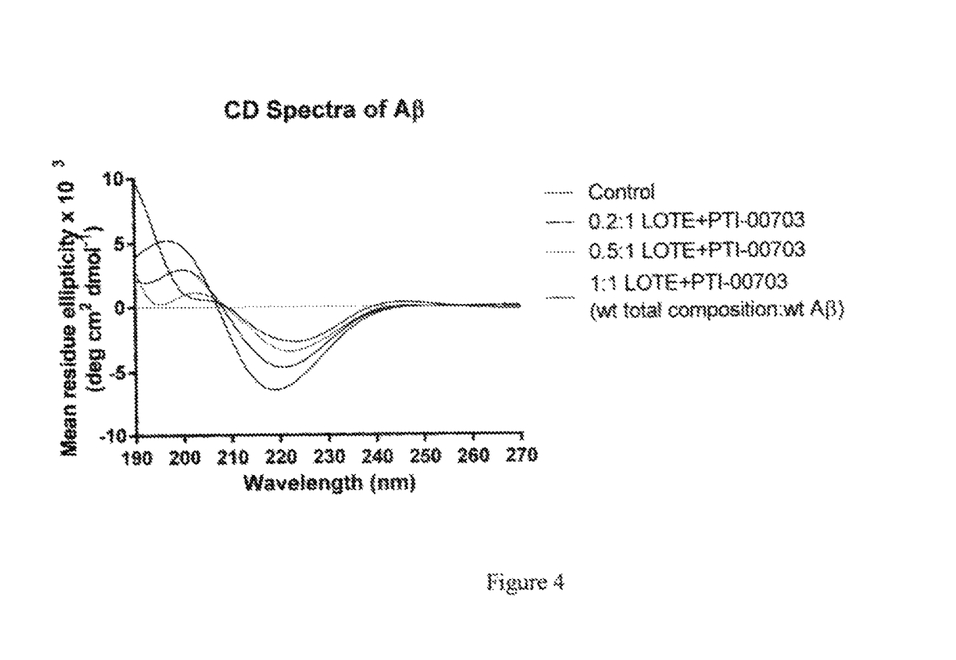
FIG. 4 Circular dichroism spectra of Aβ 1-40 after treatment with increasing concentrations of LOTE and PTI-00703®

In FIG. 4, the CD spectra of Aβ 1-40 treated with LOTE+PTI-00703® indicated a dose-dependent inhibition of β-sheet containing fibrils. A minima at 218 nm indicates the presence of β-sheet structure. A positive shift of ellipticity at 218 m indicates less β-sheet structure. At a test composition:Aβ weight ratio of 0.2:1 LOTE+PTI-00703® demonstrated 30.9% less β-sheet structure from untreated 0.5:1 LOTE+-PTI-00703® showed 53.9% less β-sheet structure than control. At equal weight equivalents (test composition:Aβ weight ratio of 1:1) there was 64.8% less β-sheet structure compared to control.

These data verified LOTE-PTI-00703® has a significant ability to inhibit abnormal assembly of Aβ into fibrillar, β-sheet assemblies and maintains Aβ 1-40 in a less pathogenic form.

Use of Recombinant Tau Repeat Domain for In Vitro Screening of Tau Aggregation Inhibitors During in vitro screening for identification of tau aggregation inhibitors, we found that under the same experimental conditions, formation of paired helical filaments (PHFs) from commercially-purchased full-length tau protein (Tau441; from rPeptide) was much slower (>11 days; data not shown) than that from the tau repeat domain (TauRD; containing Q244-E372 of Tau441) (≥24 hr) (S. Barghorn et al, Methods Mol Biol, 299:35-51, 2005).

Because of the remarkably short turn-around time and common aggregation properties, we used TauRD for in vitro screening to identify tau aggregation inhibitors in our current invention. Since the TauRD protein is not commercially available, we produced our own protein for this project. A cDNA fragment coding for the human TauRD was cloned into a bacterial expression vector and the construct was then expressed in *E. coli*. Bacterial clones demonstrating high levels of expression of TauRD were then selected for protein purification. The recombinant TauRD protein was then purified by heat-stability treatment and cation exchange chromatography as described with minor modifications (S. Barghorn et al, Methods Mol Biol, 299:35-51, 2005). Using this method, we achieved a protein yield of 20 mg per liter of bacterial culture). Aggregation and PHF formation of purified TauRD were evaluated and validated by independent assays including Thioflavin S (ThioS) fluorometry, a dye that fluorescences after binding to fibrils (FIG. 5D), circular dichroism (CD) spectroscopy, a method that detects changes in secondary structure of proteins (FIGS. 5B and 5C) and electron microscopy (FIGS. 5E-G). The results consistently demonstrate that TauRD (10 µM) is able to form ThioS-positive, β-sheet-containing PHFs when incubated with equimolar heparin (Sigma-Aldrich, St. Louis, Mo.) at 37° C., with shaking at 800-1000 rpm for ≥1 day.

Figures 5A, 5B:
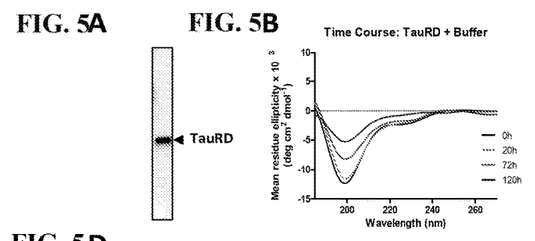
FIG. 5A-G Data from various internal tests to characterize TauRD fibrils for screening of tau aggregation inhibitors.
Figure 5C:
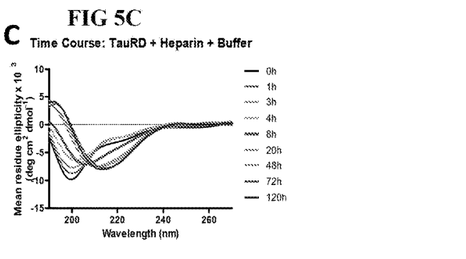
Figure 5D:
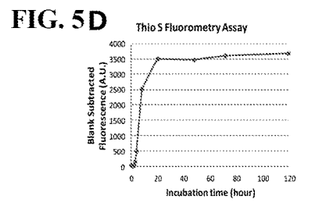
Figure 5E:
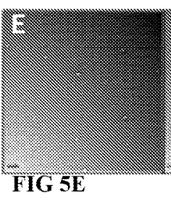
Figure 5F:
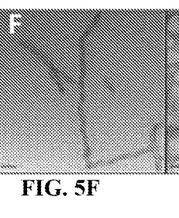
Figure 5G:
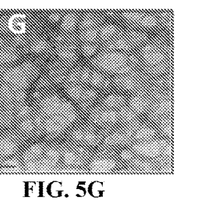

In FIG. 5A, TauRD (15 kDa) protein purified from *E. coli* was evaluated by SDS-PAGE/silver stain with typical purity of >95%. In FIG. 5B-C are examples of CD spectroscopy of non-aggregated and aggregated TauRD proteins. TauRD aggregates were prepared in the presence of equimolar (10 µM) ratios of TauRD and heparin in 20 mM sodium phosphate buffer (pH7.4), incubated at 37° C. with shaking for 0-120 h. In the absence of heparin, CD spectra of non-aggregated TauRD was random coil with ellipticity minima at 195 nm (FIG. 5B). In the presence of heparin, CD spectra showed time-dependent conformational changes of TauRD protein from random coil (minima at 195 nm) at time 0 to β-sheet (minima at 218 nm) at 20-120 h (FIG. 5C). FIG. 5D is an example of TauRD aggregation monitored by ThioS fluorometry over time. The results in FIG. 5D, show formation of ThioS-positive TauRD fibrils after 20 h incubation. In the absence of heparin without fibril formation, tauRD ThioS signals were <200 arbitrary units (A.U.) of fluorescence at all time points. Tau fibril formation was confirmed by negative stain EM in FIG. 5E-G. Representative images show formation of Tau fibrils after 48 h incubation with heparin. TauRD monomers at time 0 are shown in FIG. 5E (Bar=200 nm). Formation of TauRD fibrils at 48 hr are shown in FIGS. 5F-G (Bar=50 nm). Both straight and paired helical filaments were found.

Example 3: Identification of Novel Tau Aggregation Inhibitors by Thioflavin S Fluorometry Screening A well-known method for measuring fibril formation is Thioflavin T (ThioT) fluorometry (H. Naiki et al, Lab. Invest 65:104-110, 1991; H. Levine III, Protein Sci. 2:404-410, 1993; H. Levine III, Amyloid 2:1-6, 1995; H. Naiki and K. Nakakuki, Lab. Invest. 74:374-383, 1996). ThioT is known to bind to fibrillar proteins, and an increase in fluorescence correlates with an increase in fibril formation, whereas a decrease in fluorescence correlates with a decrease in fibrils due to disassembly and/or disruption. We modified the assay by replacing ThioT with Thioflavin S (ThioS), a related anionic dye with similar properties, because the latter has been shown to be more sensitive, and reproducible for quantifying Tau PHFs (data not shown; P. Friedhoff et. al, Biochemistry, 37(28): 10223-30, 1998). ThioS fluorometry was employed to assess whether the above described mixed compositions were capable of causing a disassembly/disruption of fibrils.

Aggregated tau fibrils were prepared in the presence of equimolar ratios of TauRD and heparin (10 µM each) in 20 mM sodium phosphate buffer, pH7.4. The reaction mixture was incubated at 37° C. with shaking (800-1000 rpm) for 24 h to 72 h. Test compositions were tested at varying weight to weight concentrations with 0.14 mg/ml TauRD with heparin. The same reaction mixtures (+increasing concentrations of test compositions) but without TauRD were also set up in parallel to serve as background controls. For all test compounds background ThioS fluorescence readings were very low, usually <5% of those of the TauRD-containing wells.

Following 24-72 h of co-incubation, 50 µl of each incubation mixture was transferred into a black 96-well microtiter plate (Santa Cruz Biotechnology, Inc., Dallas, Tex.) with 50 µl of phosphate buffered saline (PBS; Sigma-Aldrich, St Louis, Mo.) and 25 µl of Thioflavin S solution (500 mM Thioflavin S; Sigma-Aldrich, St. Louis, Mo. in PBS, pH 7.4). Using an ELISA plate fluorometer, fluorescence was read at 485 nm (444 nm excitation wavelength) after subtraction with buffer alone or composition alone, as blank.

Inhibition of tau aggregation by 50%, $IC_{50}$, was calculated using Prism version 5 software (GraphPad Software) by nonlinear regression [(Log [inhibitor] vs, normalized response; variable slope)]. In initial screenings, the test compounds demonstrated a broad range of activities for inhibiting tau protein fibril formation: $IC_{50}$ values ranged from <0.14 mg/ml (less or equal to the concentration of tauRD in the assay) to infinity (i.e. no activity at all). The results suggested that the inhibitory activities were test subject specific. A few samples were also tested for their ability to disrupt preformed tau fibrils (disruption assay).

Figure 6:
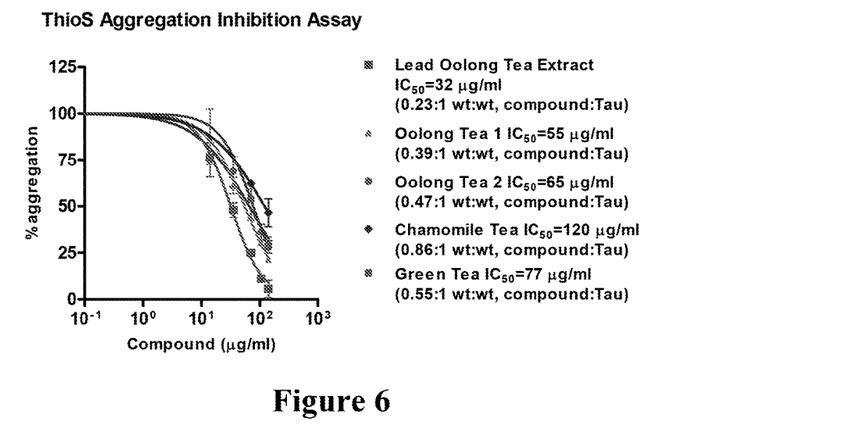
FIG. 6 A graph of tau aggregation measured by Thioflavin S fluorometry after incubation with tea extracts.

Over 25 tea extracts were tested for inhibition of ThioS-positive tau aggregates. A majority of teas were oolong tea extracts. FIG. 6, is an example of ThioS fluorescence of tau aggregated in the presence of a few oolong tea extracts, chamomile tea and green tea. Increasing concentrations of extracts were incubated with 0.14 mg/ml (10 µM) tauRD and equimolar heparin for 24-72 h, shaking at 1000 rpm, 37° C. The lead oolong tea extract (LOTE) inhibited tau aggregates more than other oolong teas, chamomile tea or green tea extract LOTE inhibited tau aggregation 50% ($IC_{50}$) with a ratio of 0.23:1, weight:weight, of composition to tau. This experiment demonstrates LOTE has a superior ability aver other compositions to inhibit abnormal assembly of tau into fibrillar, pathogenic assemblies.

Figure 7:
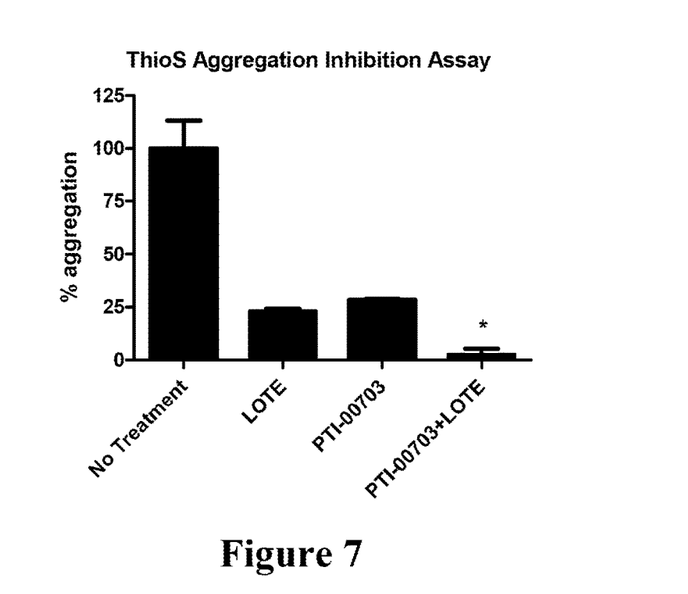
FIG. 7 A graph of tau aggregation measured by Thioflavin S fluorometry after incubation with LOTE and PTI-00703.

After identifying a tea extract that has excellent tau aggregation inhibition, lead oolong tea extract (LOTE) was incubated alone or in combination with PTI-00703® in the tau aggregation inhibition assay. A combination of specific oolong tea and PTI-00703® inhibited ThioS-positive tau aggregates more than LOTE or PTI-00703® alone (*significant by paired t-test, p<0.05) (FIG. 7). This combination of lead oolong tea extract and PTI-00703® is a potent inhibitor of tau aggregation/fibrillogenesis that could be used as a novel therapeutic for tauopathies.

Example 4: Tau Aggregation Inhibition by Lead Oolong Tea Extract Confirmed by Analysis of Protein Secondary Structure by Circular Dichroism (CD) Spectroscopy CD is a powerful method that provides dye-independent confirmation that the structure of a protein has changed. CD measures the differential absorption between left and right handed circularly polarized light. Proteins contain elements of asymmetry that exhibit distinct CD signals measured in units of ellipticity. Thioflavin S fluorescent, tau aggregates have an ellipticity minima of 218 nm, which is characteristic of β-sheet containing proteins. Non-aggregated tau has an ellipticity with a characteristic minima at 195 nm indicating random coil structure. CD spectroscopy was performed to determine each composition's potency to inhibit formats of β-sheet secondary structure in TauRD under aggregation-prone conditions. CD spectra were taken from samples containing +/– TauRD with increasing concentrations of compounds, and analyzed at 25° C. on a JASCO Model J-810 Spectropolarimeter. CD spectroscopy and ThioS assays were analysed in parallel from the same sample preparation in order to correlate the results from two independent assays.

Figure 8:
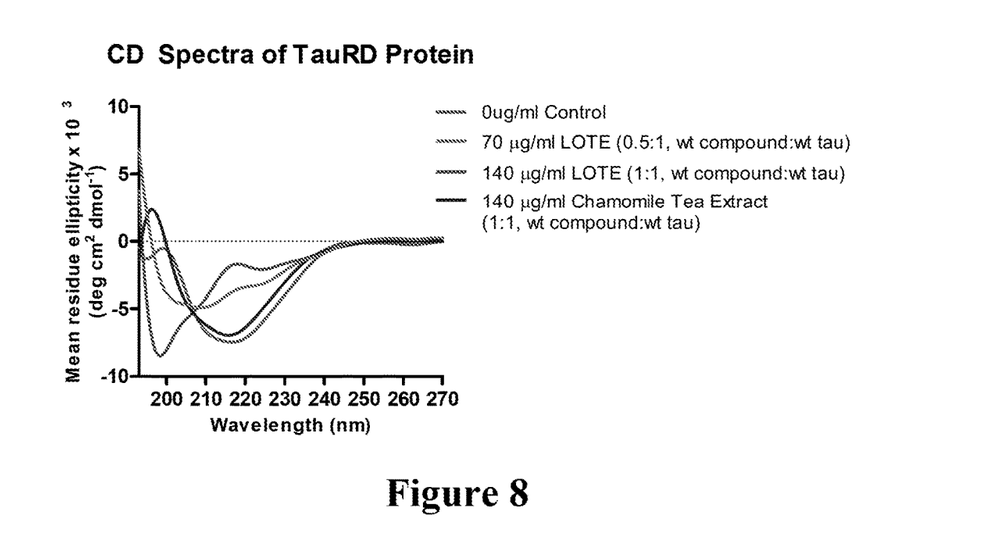
FIG. 8 A graph of tau secondary structure measured by circular dichroism spectroscopy after treatment with LOTE.

In FIG. 8, tau was treated with lead oolong tea extract (LOTE) or chamomile tea extract for 48 h. Tau treated with LOTE is dose-dependently inhibited from converting to β-sheet containing fibrils. At the highest concentration of LOTE treatment, tau remains in soluble, random coil form with a minima ~195 nm. Conversely, at the highest concentration of treatment with chamomile tea extract, tau still changes to an aggregated, β-sheet structure similar to the untreated control. These data confirm LOTE has a significant ability over other compositions to inhibit abnormal assembly of tau into fibrillar, β-sheet assemblies and maintains tau in a non-pathogenic soluble, random coil form.

Example 5: Inhibition of Tau Protein Fibrillogenesis and Disaggregation of Preformed Tau Fibrils by PTI-00703+LOTE Determined by Negative Stain Electron Microscopy (EM)

EM analysis was used to independently monitor the effectiveness of compositions to inhibit tau fibrillogenesis. In these experiments, tau fibrils were assembled by incubating equimolar ratios of TauRD protein and heparin (10 μM each) in the absence (control) or presence of increasing concentrations of test compositions. After the 2-day incubation, samples were spotted onto grids, stained with 2% uranyl acetate, and visualized at 8,000× to 30,000× magnifications with a JEOL 1010 transmission electron microscope.

Figure 9:
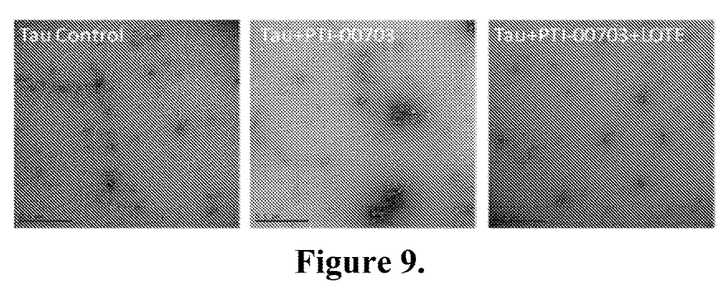
FIG. 9 Electron micrographs of tau fibril formation with PTI-0073 and LOTE.

In FIG. 9, left panel, EM analysis confirmed formation of tau fibrils in the absence of treatment. Without treatment, tau formed a mixture of paired straight and helical filaments similar to those found in human tauopathies (V. M. Lee et al., Ann. Rev. Neurosci. 24:1121-159, 2001). These samples were also tested by the ThioS assay and CD and confirmed to be ThioS-fluorescence positive and β-sheet in structure. In the presence of PTI-00703® and PTI-00703®+LOTE (FIG. 9, middle and right panel), tau fibrils become shortened and sparse, indicating an inhibition of tau fibril formation. Even less fibrils are apparent in tau samples treated with both PTI-00703® and LOTE. These results correlate well with ThioS fluorometry and CD analysis, which showed a reduction in ThioS fluorescence and decrease in β-sheet structure. Using three independent methodologies, we have identified and validated PTI-00703+lead oolong tea extract as a potent inhibitor of tau aggregation/fibrillogenesis.

Figure 10:
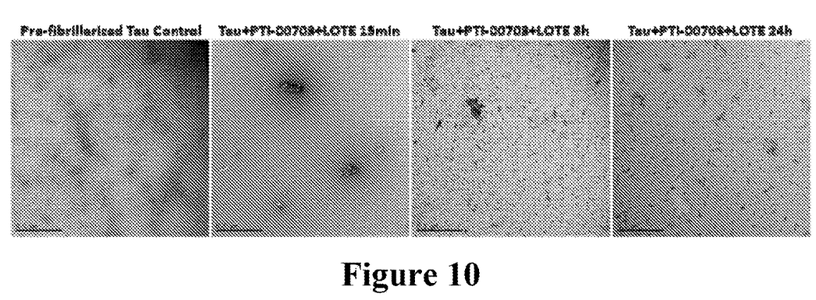
FIG. 10 Electron micrographs of preformed tau fibrils treated with PTI-00703 and LOTE.

Utilizing EM analysis, preformed tau fibrils were shown to rapidly disaggregate in the presence of both PTI-00703® and LOTE. TauRD was incubated with equimolar heparin to form fibrils as described in the previous assay. TauRD was diluted with or without test compositions and incubated, shaking at 37° C. for various time points. At each time point tauRD+/− test compounds was assayed for ThioS fluorescence and snap frozen for EM analysis. In FIG. 10 (left panel) without treatment, pre-fibrillarized tau remained in long filaments. In the next panels, pre-fibrillarized tau was found to rapidly disaggregate in the presence of PTI-00703®+LOTE. As early as 15 minutes incubation with PTI-00703®+LOTE, tau fibrils are shorter and sparser than without treatment. Disruption of tau fibrils was also confirmed by ThioS assay (data not shown). These data indicate the composition of PTI-00703®+LOTE not only can inhibit tau aggregation but can disaggregate preformed tau fibrils.

Example 6: Further In Vivo Testing of the PTI-00703®+LOTE for Improvement of Cognition and Memory Further in vivo studies are used to test the PTI-00703®+LOTE plant extract combination for their effectiveness in the reduction of brain "plaque and tangle" load and improvement of cognition and memory. 40-60 men and women are selected for a clinical study. Subjects have age-associated memory impairment (AAMI), and expecting to have worsening symptoms of memory loss within the 6-month study period, but are in good general health otherwise.

This study includes a placebo group, i.e. the subjects are divided into two groups, one of which receives the PTI-00703®+oolong tea extract, combination capsules (two 390 mg capsules containing the PTI-00703®+oolong tea extract in a 1:1 weight/weight combination with a meal; preferably lunch) of this disclosure, and the other receives a placebo (two capsules containing capsules without the study product active ingredients). The patients are benchmarked as to memory, cognition, focus, concentration, reasoning and other symptoms associated with mild-cognitive impairment (MCI). Subjects in the test groups receive a therapeutic dose of the combination study product extract or placebo for 6 months, with analysis for short-term memory, cognition, focus and concentration to be examined at 0, 1, 3, and 6-months of treatment. Accurate records with regards to memory, focus and concentration are kept as to the benchmarked symptoms in both groups and at the end of the study these results are compared. The results also are compared between members of each group. In addition, the results for each patient are compared to the symptoms reported by each patient before the study began. Activity of the combination PTI-00703®+oolong tea extract study product is illustrated by the attenuation of the typical cognitive decline, decline in short-term memory, cognition, focus and concentration, and/or associated behavioral disruptions associated with age-associated memory impairment (AAMI)

All references and patent publications provided herein are hereby incorporated by reference in their entireties.

We claim:

1. A composition comprising a therapeutically effective amount of an *Uncaria tomentosa* extract in combination with an oolong tea extract formulated for oral administration in a capsule.

2. The composition of claim 1, wherein the capsule contains 100-500 mg of the *Uncaria tomentosa* extract and 100-500 mg of the oolong tea extract.

3. The composition of claim 1, wherein the capsule is a 200-1000 mg capsule.

4. The composition of claim 1, wherein the capsule is a hard or soft gelatin or vegetarian capsule.

5. The composition of claim 1, wherein the *Uncaria tomentosa* extract and the oolong tea extract are in the form of a lyophilized powder.

* * * * *